(12) United States Patent
Bishop et al.

(10) Patent No.: US 12,336,894 B2
(45) Date of Patent: Jun. 24, 2025

(54) ABSORBENT ARTICLE WITH WAIST CONTAINMENT MEMBER AND METHOD OF MANUFACTURING THEREOF

(71) Applicant: Kimberly-Clark Worldwide, Inc., Neenah, WI (US)

(72) Inventors: David F. Bishop, Appleton, WI (US); Patsy A. Benedict, Omro, WI (US); Joseph D. Coenen, Kaukauna, WI (US); Kaitlyn E. Mast, Shipshewana, IN (US); Michael J. Faulks, Neenah, WI (US); Thomas Roessler, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 995 days.

(21) Appl. No.: 17/381,717

(22) Filed: Jul. 21, 2021

(65) Prior Publication Data

US 2021/0346212 A1 Nov. 11, 2021

Related U.S. Application Data

(63) Continuation of application No. 15/557,895, filed as application No. PCT/US2015/023596 on Mar. 31, 2015, now Pat. No. 11,096,836.

(51) Int. Cl.
*A61F 13/49* (2006.01)
*A61F 13/494* (2006.01)
*A61F 13/495* (2006.01)

(52) U.S. Cl.
CPC .... *A61F 13/49011* (2013.01); *A61F 13/4942* (2013.01); *A61F 13/49473* (2013.01); *A61F 13/495* (2013.01); *A61F 2013/4958* (2013.01)

(58) Field of Classification Search
CPC ............ A61F 13/49011; A61F 13/4942; A61F 13/49473; A61F 13/495; A61F 2013/4958; A61F 13/49466
See application file for complete search history.

(56) References Cited

U.S. PATENT DOCUMENTS

| 3,395,708 A | 8/1968 | Laurence et al. |
| 3,800,796 A | 4/1974 | Jacob |

(Continued)

FOREIGN PATENT DOCUMENTS

| CN | 1200662 A | 12/1998 |
| CN | 1853592 A | 11/2006 |

(Continued)

*Primary Examiner* — Jessica Arble
(74) *Attorney, Agent, or Firm* — KIMBERLY-CLARK WORLDWIDE, INC.

(57) ABSTRACT

An absorbent article (10, 110, 210) can include a waist containment member (54) with a first longitudinal side edge (72), a second longitudinal side edge (74), a proximal portion (76), and a distal portion (78). A fold (79a) can separate the proximal portion (76) from the distal portion (78). The proximal portion (76) can be coupled to the chassis (11) and the distal portion (78) can be configured to freely move with respect to the chassis (11) when the absorbent article (10, 110, 210) is in a relaxed configuration to provide a containment pocket (82). The absorbent article (10, 110, 210) can include a pair of containment flaps (50, 52). The containment flaps (50, 52) can each include a base portion (64) and a projection portion (66).

18 Claims, 15 Drawing Sheets

(56) References Cited

U.S. PATENT DOCUMENTS

| | | | |
|---|---|---|---|
| 3,848,594 | A | 11/1974 | Buell |
| 3,860,003 | A | 1/1975 | Buell |
| 3,930,501 | A | 1/1976 | Schaar |
| 3,978,861 | A | 9/1976 | Schaar |
| 3,995,640 | A | 12/1976 | Schaar |
| 4,074,716 | A | 2/1978 | Schaar |
| 4,525,407 | A | 6/1985 | Ness |
| 4,642,110 | A | 2/1987 | Dudek |
| 4,643,729 | A | 2/1987 | Laplanche |
| 4,657,539 | A | 4/1987 | Hasse |
| 4,657,802 | A | 4/1987 | Morman |
| 4,681,579 | A | 7/1987 | Toussant et al. |
| 4,735,624 | A | 4/1988 | Mazars |
| 4,738,677 | A | 4/1988 | Foreman |
| 4,741,949 | A | 5/1988 | Morman et al. |
| 4,753,646 | A | 6/1988 | Enloe |
| 4,808,176 | A | 2/1989 | Kielpikowski |
| 4,808,177 | A | 2/1989 | DesMarais et al. |
| 4,822,435 | A | 4/1989 | Igaue et al. |
| 4,850,990 | A | 7/1989 | Huntoon et al. |
| 4,935,021 | A | 6/1990 | Huffman et al. |
| 4,938,755 | A | 7/1990 | Foreman |
| 4,977,011 | A | 12/1990 | Smith |
| 5,026,364 | A | 6/1991 | Robertson |
| 5,064,421 | A | 11/1991 | Tracy |
| 5,069,672 | A | 12/1991 | Wippler et al. |
| 5,106,385 | A | 4/1992 | Allen et al. |
| 5,151,091 | A | 9/1992 | Glaug et al. |
| 5,151,092 | A | 9/1992 | Buell et al. |
| 5,187,817 | A | 2/1993 | Zolner |
| 5,209,801 | A | 5/1993 | Smith |
| 5,366,452 | A | 11/1994 | Widlund et al. |
| 5,397,318 | A | 3/1995 | Dreier |
| 5,413,570 | A | 5/1995 | Enloe |
| 5,439,459 | A | 8/1995 | Tanji et al. |
| 5,451,219 | A | 9/1995 | Suzuki et al. |
| 5,514,104 | A | 5/1996 | Cole et al. |
| 5,514,121 | A | 5/1996 | Roe et al. |
| 5,531,730 | A | 7/1996 | Dreier |
| 5,540,671 | A | 7/1996 | Dreier |
| 5,558,660 | A | 9/1996 | Dreier |
| 5,558,661 | A | 9/1996 | Roe et al. |
| 5,569,227 | A | 10/1996 | Vandemoortele et al. |
| 5,582,606 | A | 12/1996 | Bruemmer et al. |
| 5,593,401 | A | 1/1997 | Sosalla et al. |
| 5,624,422 | A | 4/1997 | Allen |
| 5,643,242 | A | 7/1997 | Lavon et al. |
| 5,649,918 | A | 7/1997 | Schleinz |
| 5,667,503 | A | 9/1997 | Roe et al. |
| 5,672,166 | A | 9/1997 | Vandemoortele |
| 5,674,215 | A | 10/1997 | Ronnberg |
| 5,685,873 | A | 11/1997 | Bruemmer |
| 5,690,627 | A | 11/1997 | Clear et al. |
| 5,695,488 | A | 12/1997 | Sosalla |
| 5,776,121 | A | 7/1998 | Roe et al. |
| 5,795,347 | A | 8/1998 | Roe et al. |
| 5,817,086 | A | 10/1998 | Kling |
| 5,827,259 | A | 10/1998 | Laux et al. |
| 5,858,012 | A | 1/1999 | Yamaki et al. |
| 5,895,382 | A | 4/1999 | Popp et al. |
| 5,904,675 | A | 5/1999 | Laux et al. |
| 5,931,826 | A | 8/1999 | Faulks et al. |
| 5,938,652 | A | 8/1999 | Sauer |
| 5,993,433 | A | 11/1999 | St. Louis et al. |
| 6,103,952 | A | 8/2000 | Coles et al. |
| 6,132,410 | A | 10/2000 | Van Gompel et al. |
| 6,135,988 | A | 10/2000 | Turner et al. |
| 6,142,985 | A | 11/2000 | Feist |
| 6,149,638 | A | 11/2000 | Vogt et al. |
| 6,174,303 | B1 | 1/2001 | Suprise et al. |
| 6,217,563 | B1 | 4/2001 | Van Gompel et al. |
| 6,258,076 | B1* | 7/2001 | Glaug .................. A61F 13/532 604/386 |
| 6,264,639 | B1 | 7/2001 | Sauer |
| 6,264,641 | B1 | 7/2001 | Van Gompel et al. |
| 6,280,426 | B1 | 8/2001 | Turner et al. |
| 6,293,937 | B2 | 9/2001 | Matsushita et al. |
| 6,306,122 | B1 | 10/2001 | Narawa et al. |
| 6,315,764 | B1 | 11/2001 | Faulks et al. |
| 6,425,889 | B1 | 7/2002 | Kitaoka et al. |
| 6,443,933 | B1 | 9/2002 | Suzuki et al. |
| 6,455,753 | B1 | 9/2002 | Glaug et al. |
| 6,458,114 | B1 | 10/2002 | Mishima et al. |
| 6,482,194 | B1 | 11/2002 | Putzer |
| 6,491,677 | B1 | 12/2002 | Glaug et al. |
| 6,494,872 | B1 | 12/2002 | Suzuki et al. |
| 6,506,185 | B1* | 1/2003 | Sauer .................. A61F 13/49466 604/385.101 |
| 6,527,756 | B1 | 3/2003 | Mishima et al. |
| 6,638,262 | B2 | 10/2003 | Suzuki et al. |
| 6,648,870 | B2 | 11/2003 | Itoh et al. |
| 6,699,228 | B1 | 3/2004 | Chmielewski et al. |
| 6,827,806 | B2 | 12/2004 | Uitenbroek et al. |
| 6,838,591 | B2 | 1/2005 | Waksmundzki et al. |
| 6,881,207 | B1 | 4/2005 | Tracy |
| 6,890,327 | B2 | 5/2005 | Suzuki et al. |
| 7,066,921 | B2 | 6/2006 | Schmoker et al. |
| 7,166,093 | B2 | 1/2007 | Drevik et al. |
| 7,166,095 | B1 | 1/2007 | Coates |
| 7,247,152 | B2 | 7/2007 | Klemp et al. |
| 7,604,625 | B2 | 10/2009 | Turi et al. |
| 7,666,173 | B2 | 2/2010 | Mishima et al. |
| 7,767,876 | B2 | 8/2010 | Davis et al. |
| 7,842,021 | B2 | 11/2010 | Wood et al. |
| 7,879,017 | B1 | 2/2011 | Tabata et al. |
| 7,993,314 | B2 | 8/2011 | Asp et al. |
| 8,075,543 | B2 | 12/2011 | Okuda |
| 9,044,359 | B2 | 6/2015 | Wciorka et al. |
| 10,010,458 | B2 | 7/2018 | Barnes |
| 10,159,610 | B2 | 12/2018 | Barnes |
| 11,096,836 | B2 | 8/2021 | Bishop et al. |
| 2001/0016720 | A1 | 8/2001 | Otsubo |
| 2002/0045878 | A1 | 4/2002 | Shimoe et al. |
| 2002/0082570 | A1 | 6/2002 | Mishima et al. |
| 2002/0147438 | A1 | 10/2002 | Tanaka et al. |
| 2003/0045853 | A1 | 3/2003 | Sauer |
| 2003/0050616 | A1 | 3/2003 | Reynolds et al. |
| 2003/0109844 | A1 | 6/2003 | Gibbs |
| 2003/0119405 | A1 | 6/2003 | Abuto et al. |
| 2003/0216705 | A1 | 11/2003 | Coates |
| 2004/0002690 | A1 | 1/2004 | Miyamoto |
| 2004/0019343 | A1 | 1/2004 | Olson et al. |
| 2004/0127882 | A1 | 7/2004 | Weber |
| 2004/0243086 | A1 | 12/2004 | VanGompel et al. |
| 2005/0027274 | A1 | 2/2005 | Suzuki et al. |
| 2005/0148974 | A1 | 7/2005 | Datta et al. |
| 2005/0215974 | A1 | 9/2005 | Susan |
| 2005/0256488 | A1 | 11/2005 | Sperl |
| 2006/0058738 | A1 | 3/2006 | Ponzi et al. |
| 2006/0058767 | A1 | 3/2006 | Zhang et al. |
| 2007/0093164 | A1 | 4/2007 | Nakaoka |
| 2007/0112322 | A1 | 5/2007 | Ashton et al. |
| 2007/0255245 | A1 | 11/2007 | Asp et al. |
| 2007/0293832 | A1 | 12/2007 | Wood et al. |
| 2008/0300560 | A1 | 12/2008 | Magnusson et al. |
| 2010/0305533 | A1 | 12/2010 | Ashton et al. |
| 2012/0277703 | A1 | 11/2012 | Rhein et al. |
| 2012/0323207 | A1 | 12/2012 | Takaishi |
| 2013/0012905 | A1 | 1/2013 | Katsuragawa et al. |
| 2013/0012906 | A1 | 1/2013 | Takino |
| 2013/0012907 | A1 | 1/2013 | Sasayama et al. |
| 2013/0046266 | A1 | 2/2013 | Kawakami |
| 2014/0018761 | A1 | 1/2014 | Orchard, IV et al. |
| 2014/0121623 | A1 | 5/2014 | Kirby et al. |
| 2014/0128829 | A1 | 5/2014 | Miyake et al. |
| 2014/0257231 | A1 | 9/2014 | Wang et al. |
| 2014/0350504 | A1 | 11/2014 | Popp et al. |
| 2015/0051568 | A1 | 2/2015 | Sakaguchi et al. |
| 2015/0182388 | A1 | 7/2015 | Katsuragawa et al. |
| 2017/0000658 | A1 | 1/2017 | Chatterjee et al. |
| 2017/0128281 | A1* | 5/2017 | Takino .................. A61F 13/495 |
| 2017/0239104 | A1 | 8/2017 | Jang et al. |
| 2017/0246054 | A1 | 8/2017 | Bishop et al. |
| 2017/0296401 | A1 | 10/2017 | Sugiyama et al. |

(56) References Cited

U.S. PATENT DOCUMENTS

| | | |
|---|---|---|
| 2018/0055698 A1 | 3/2018 | Bishop et al. |
| 2018/0071155 A1 | 3/2018 | Bishop et al. |
| 2018/0104116 A1 | 4/2018 | Bishop et al. |
| 2019/0083331 A1 | 3/2019 | Barnes |
| 2020/0038256 A1 | 2/2020 | Jang et al. |
| 2020/0107973 A1 | 4/2020 | Bishop et al. |

FOREIGN PATENT DOCUMENTS

| | | |
|---|---|---|
| CN | 102065811 A | 5/2011 |
| CN | 102065813 B | 11/2014 |
| CN | 204072501 U | 1/2015 |
| JP | 2001178772 A | 7/2001 |
| JP | 4754634 B2 | 8/2011 |
| KR | 100648562 B1 | 11/2006 |
| KR | 2020130001181 U | 2/2013 |
| WO | 9601607 A1 | 1/1996 |
| WO | 0037008 A1 | 6/2000 |
| WO | 2013021897 A1 | 2/2013 |
| WO | 2016159983 A1 | 10/2016 |

\* cited by examiner

ABSORBENT ARTICLE WITH WAIST CONTAINMENT MEMBER AND METHOD OF MANUFACTURING THEREOF

RELATED APPLICATIONS

The present application is a continuation application and claims priority to U.S. patent application Ser. No. 15/557,895, filed on Sep. 13, 2017, which is a national-phase entry, under 35 U.S.C. § 371, of PCT Patent Application No. PCT/US15/23596, filed on Mar. 31, 2015, all of which are incorporated herein by reference.

TECHNICAL FIELD

The present disclosure relates to absorbent articles.

BACKGROUND OF THE DISCLOSURE

A primary function of personal care absorbent articles is to absorb and retain body exudates such as urine, fecal material, blood, and menses with additional desired attributes including low leakage of the exudates from the absorbent article and a dry feel to the wearer of the absorbent article. By preventing leakage of the exudates from the absorbent article, the absorbent article intends to prevent the body exudates from soiling or contaminating a wearer's or caregiver's clothing or other articles, such as bedding, that can come in contact with the wearer.

One common mode of failure is for exudates to leak out of the rear waist region or the front waist region of an absorbent article. As one example, fecal material that is not absorbed or contained by the absorbent article can move past the gaps between the absorbent article and the wearer's skin in the rear waist region and soil or contaminate the wearer's skin and clothing near their back. This may be more common of an occurrence for semi-solid fecal material, such as low viscosity fecal material, which can be prevalent with younger children. Such exudates can move around on the bodyside liner of an absorbent article under the influence of gravity, motion, force, and pressure by the wearer of the absorbent article. In such a circumstance, not only does the wearer's absorbent article need to be changed, but the wearer's clothing and/or bedding often also needs to be changed, resulting in additional work, expense, and stress for the caregiver.

Attempts have been made in the past to provide containment systems, especially on the bodyside liner or near the rear waist region to solve the problems described above. One example is by providing a waist elastic member and not adhering a portion of the waist containment member closest to the lateral axis of the absorbent article to the bodyside liner, such that the non-adhered portion of the waist elastic member can provide a containment pocket for exudates. One example of this configuration is a HUGGIES® Little Snugglers diaper. Although absorbent articles with such containment members intend to prevent leakage of exudates and have functioned adequately, failures can still occur.

Thus, there is a desire for improvements to containment systems and containment members of absorbent articles to prevent leakage of exudates, especially in the waist regions of the absorbent article. There is also a desire for improvements in containment systems to have increased void volumes to hold body exudates until the absorbent article can be changed.

SUMMARY OF THE DISCLOSURE

In one embodiment, an absorbent article can include a front waist region, a rear waist region, a crotch region, a longitudinal axis and a lateral axis. The absorbent article can include a chassis including an absorbent body. The chassis can include a body facing surface and a garment facing surface. The absorbent article can also include a pair of containment flaps including a first containment flap and a second containment flap. The first containment flap can be on a first side of the longitudinal axis and the second containment flap can be on a second side of the longitudinal axis. The first and second containment flap can each comprise a base portion including a proximal end and a distal end and a projection portion configured to extend away from the body facing surface of the chassis in at least the crotch region when the absorbent article is in a relaxed configuration. The absorbent article can further include a waist containment member disposed on the body facing surface of the chassis. The waist containment member can comprise a first longitudinal side edge and a second longitudinal side edge. The first longitudinal side edge can be disposed laterally outward of the proximal end of the base portion of the first containment flap. The second longitudinal side edge can be disposed laterally outward of the proximal end of the base portion of the second containment flap. The waist containment member can further comprise a proximal portion and a distal portion. The proximal portion can be coupled to the body facing surface of the chassis. A fold can separate the distal portion from the proximal portion. The distal portion of the waist containment member can be free to move with respect to the chassis when the absorbent article is in the relaxed configuration.

In another embodiment, an absorbent article can include a front waist region, a rear waist region, a crotch region, a longitudinal axis and a lateral axis. The absorbent article can comprise a chassis including an absorbent body. The chassis can include a body facing surface and a garment facing surface. The absorbent article can further include a waist containment member disposed on the body facing surface of the chassis. The waist containment member can comprise a first longitudinal side edge and a second longitudinal side edge. The first longitudinal side edge can be disposed on a first side of the longitudinal axis and the second longitudinal edge can be disposed on a second side of the longitudinal axis. The waist containment member can further comprise a proximal portion and a distal portion. The proximal portion can be coupled to the body facing surface of the chassis. A fold can separate the distal portion from the proximal portion. The distal portion of the waist containment member can be free to move with respect to the chassis. The waist containment member can include a first width in the lateral direction and the chassis can include a second width in the lateral direction. A ratio of the first width to the second width can be about 0.85 to about 1.00.

In yet another embodiment, a folded absorbent article can include a front waist region, a rear waist region, a crotch region, a longitudinal axis and a lateral axis. The folded absorbent article can include a chassis including an absorbent body. The chassis can include a body facing surface and a garment facing surface. The folded absorbent article can further include a pair of longitudinally extending fold lines including a first longitudinally extending fold line and a second longitudinally extending fold line. The first longitudinally extending fold line can be on a first side of the longitudinal axis and the second longitudinally extending fold line can be on a second side of the longitudinal axis. The folded absorbent article can further comprise a waist containment member disposed on the body facing surface of the chassis. The waist containment member can include a first longitudinal side edge and a second longitudinal side edge.

The first longitudinal side edge can be disposed laterally outward of the first longitudinally extending fold line and the second longitudinal side edge can be disposed laterally outward of the second longitudinally extending fold line. The waist containment member can further comprise a proximal portion and a distal portion. The proximal portion can be coupled to the body facing surface of the chassis. A fold can separate the distal portion from the proximal portion. The distal portion of the waist containment member can be free to move with respect to the chassis.

In another embodiment, a method of manufacturing an absorbent article is provided. The absorbent article can include a front waist region, a rear waist region, a crotch region, a longitudinal axis and a lateral axis. The method can include providing an absorbent assembly including a bodyside liner, an outer cover, and an absorbent body disposed between the bodyside liner and the outer cover. The absorbent assembly can include a body facing surface. The method can also include providing a pair of containment flaps including a first containment flap and a second containment flap. The first containment flap and the second containment flap can each include a base portion and a projection portion. The method can further include bonding the base portion of each of the first and the second containment flaps to the body facing surface of the absorbent assembly. The base portion of each of the first and the second containment flaps can include a proximal end and a distal end. The method can include providing a continuous web of waist containment member material and folding at least a portion of the continuous web of waist containment member material upon itself. Also, the method can include cutting the continuous web of waist containment member material to provide a waist containment member including a proximal portion, a distal portion, a first longitudinal side edge, and a second longitudinal side edge. The folding of the at least a portion of the continuous web of waist containment member material can provide a separation between the distal portion of the waist containment member and the proximal portion of the waist containment member. The method can further include bonding the proximal portion of the waist containment member to the body facing surface of the absorbent assembly such that the first longitudinal side edge of the waist containment member is disposed laterally outward of the proximal end of the base portion of the first containment flap and the second longitudinal side edge of the waist containment member is disposed laterally outward of the proximal end of the base portion of the second containment flap. The distal portion of the waist containment member can be free to move with respect to the proximal portion of the waist containment member when the absorbent article is in the relaxed configuration.

BRIEF DESCRIPTION OF DRAWINGS

A full and enabling disclosure thereof, directed to one of ordinary skill in the art, is set forth more particularly in the remainder of the specification, which makes reference to the appended figures in which.

Figure 1:
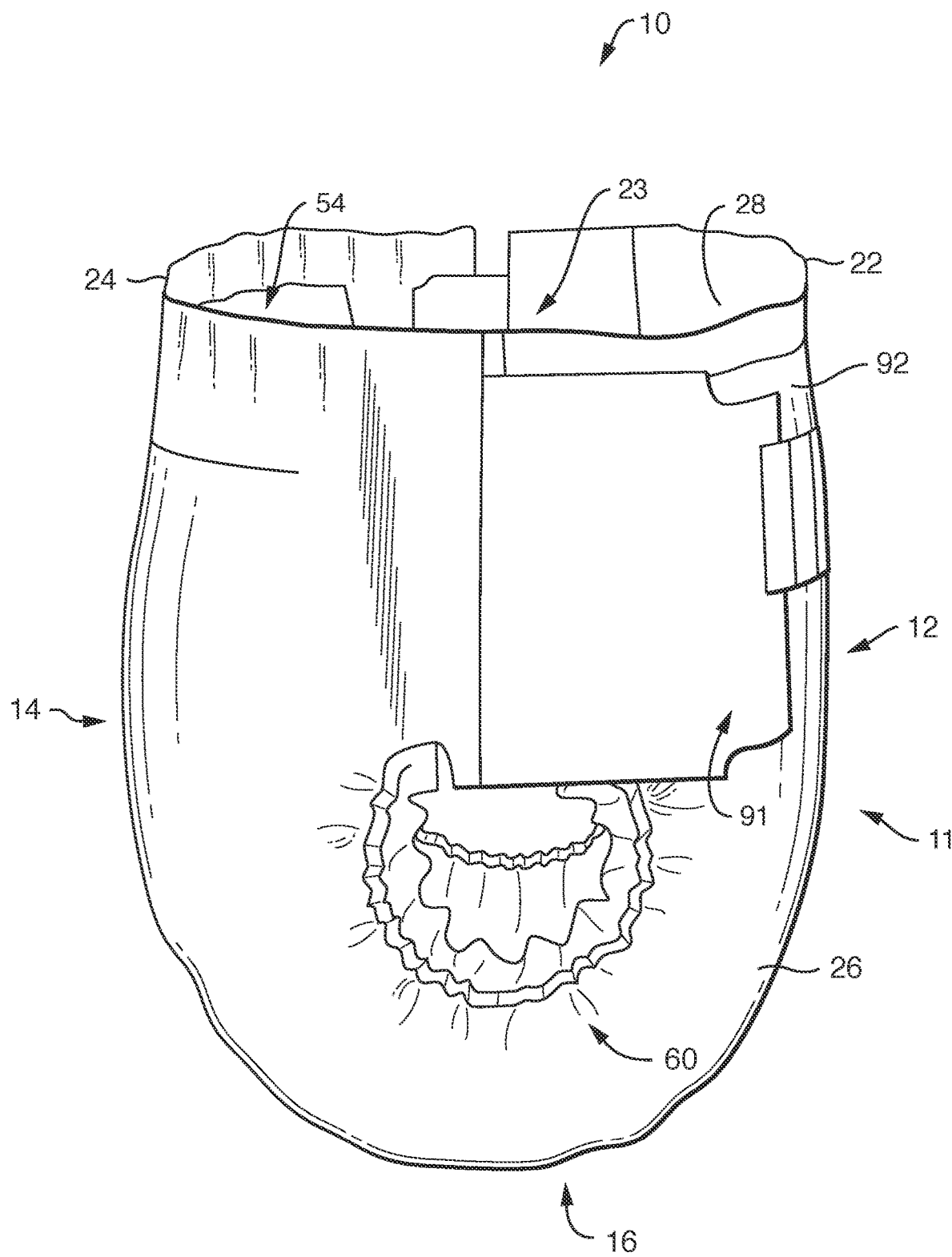
FIG. 1 is side perspective view of an exemplary embodiment of an absorbent article, such as a diaper, in a fastened condition.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards an absorbent article having a waist containment member. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Absorbent Article:

Referring to FIGS. 1-8, a non-limiting illustration of an absorbent article 10, 110, for example, a diaper, is illustrated. Other embodiments of the absorbent article could include training pants, youth pants, adult incontinence garments, and feminine hygiene articles. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure. For example, the absorbent article 210 in FIGS. 9 and 10 provides an exemplary embodiment of an absorbent article 210 that can be manufactured in cross-direction manufacturing process.

Figure 2:
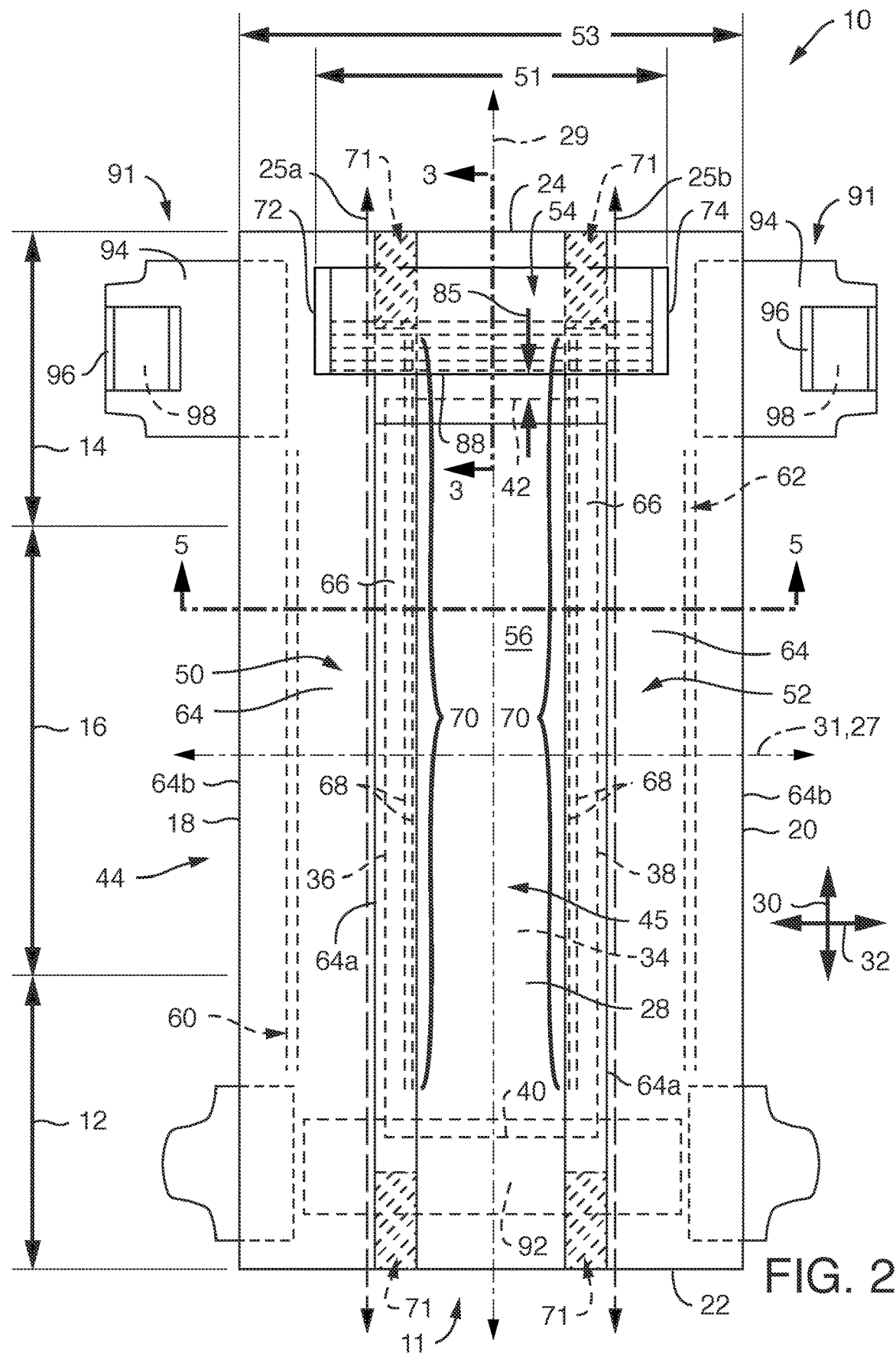
FIG. 2 is a top plan view of the absorbent article of FIG. 1 in a stretched, laid flat, unfastened condition.
Figure 6:
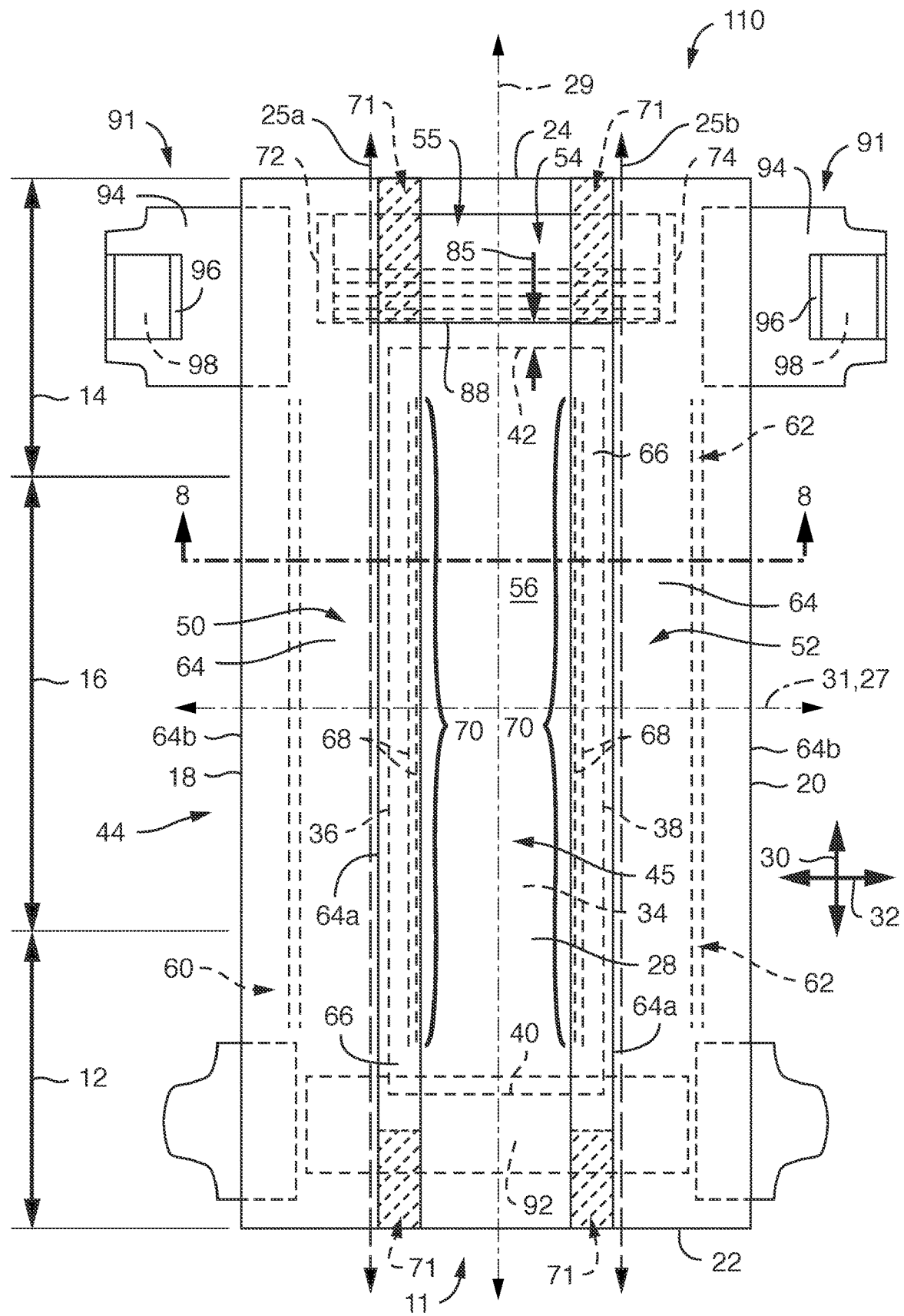
FIG. 6 is a top plan view of an alternative embodiment of an absorbent article, such as a diaper, in a stretched, laid flat, unfastened condition.
Figure 9:
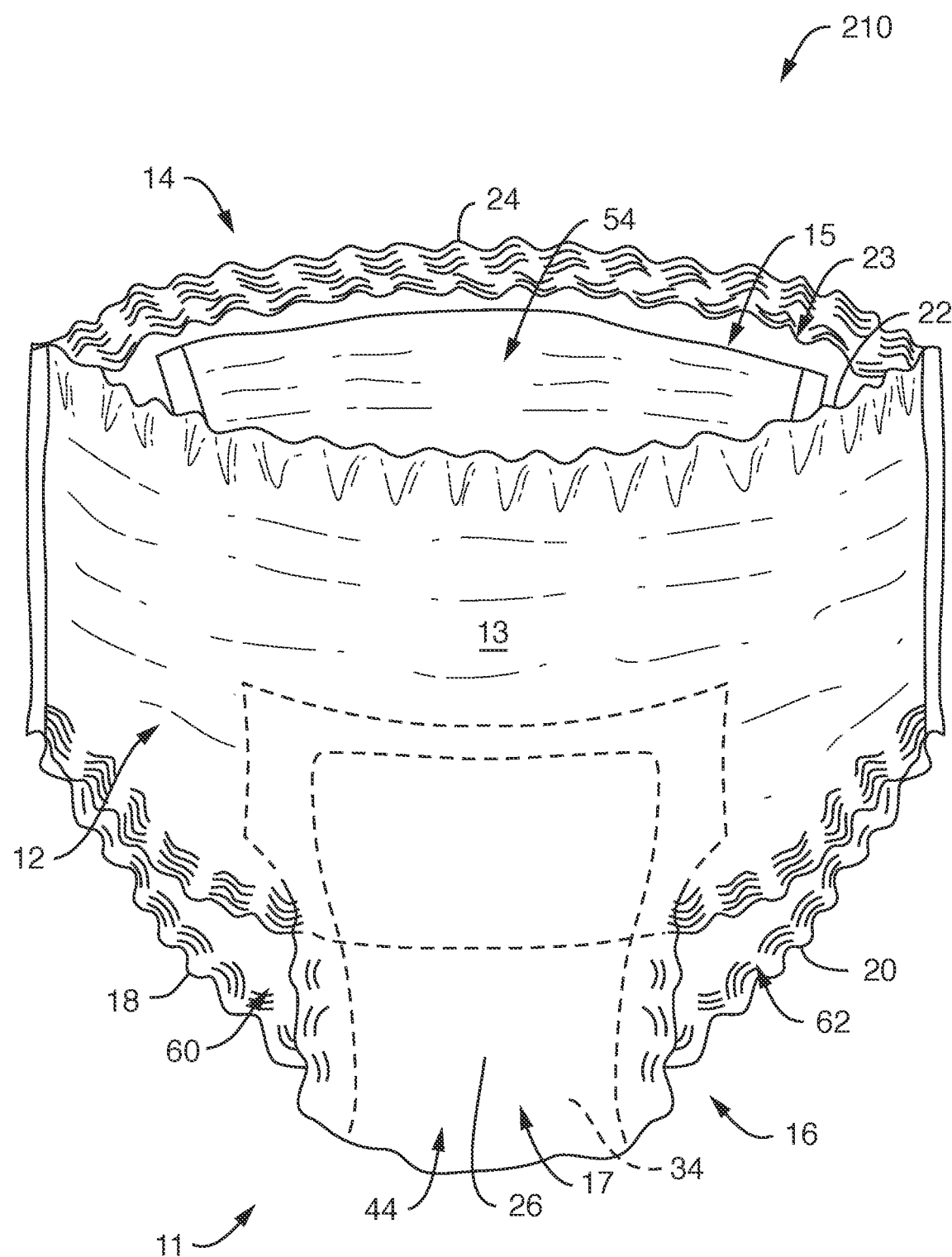
FIG. 9 is a front perspective view of an alternative embodiment of an absorbent article, such as a pant.
Figure 10:
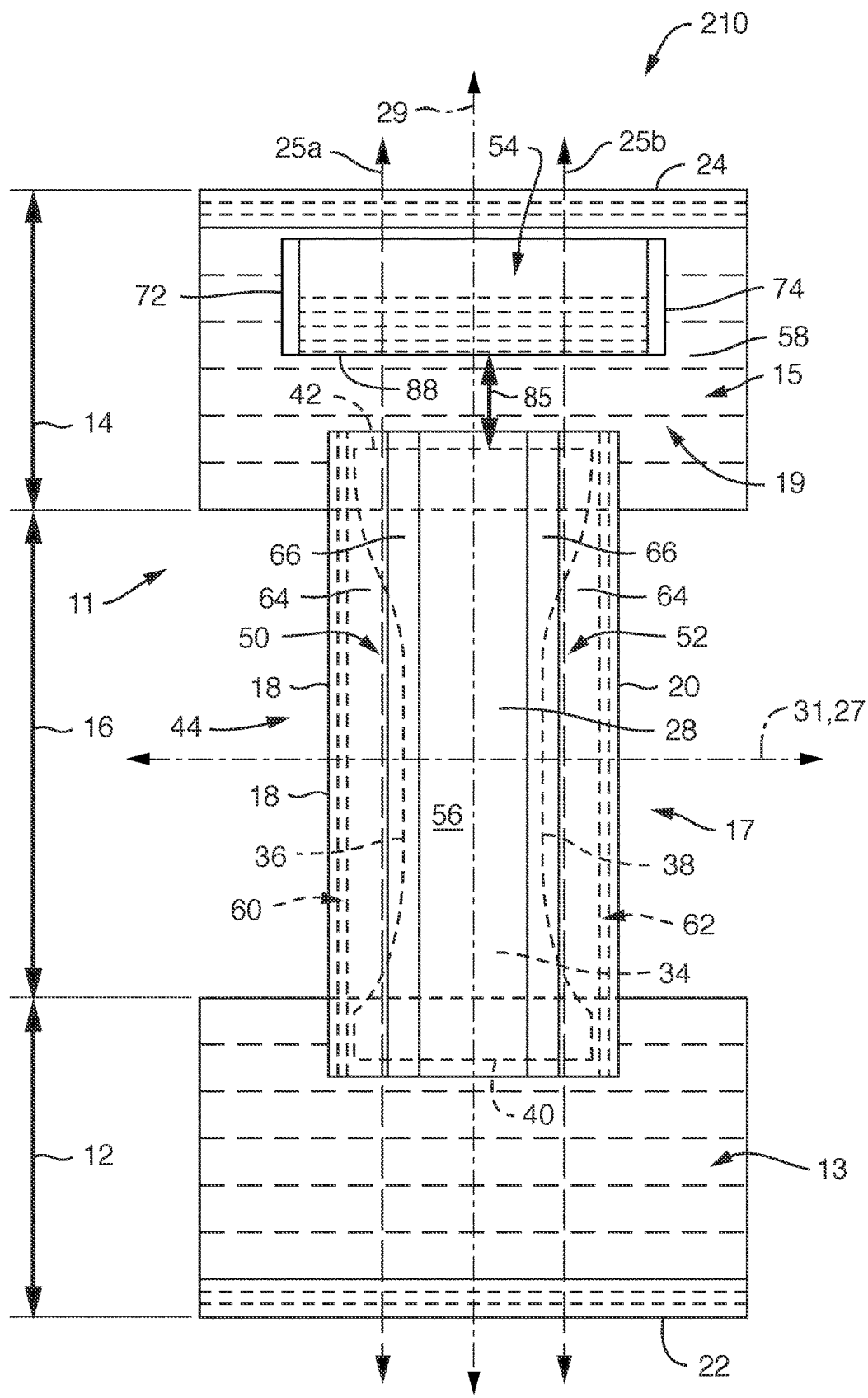
FIG. 10 is a top plan view of the absorbent article of FIG. 9 in a stretched, laid flat condition.

The absorbent article 10 illustrated in FIGS. 1 and 2, the absorbent article 110 in FIG. 6, and the absorbent article 210 illustrated in FIGS. 9 and 10 can each include a chassis 11. The absorbent article 10, 110, 210 can include a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region. In the embodiment depicted in FIGS. 9 and 10, a three-piece construction of an absorbent article 210 is depicted where the absorbent article 210 can have a chassis 11 including a front waist panel 13 defining the front waist region 12, a rear waist panel 15 defining the rear waist region 14, and an absorbent panel 17 defining the crotch region 16 of the absorbent article 210. The absorbent panel 17 can extend between the front waist panel 13 and the rear waist panel 15. In some embodiments, the absorbent panel 17 can overlap the front waist panel 13 and the rear waist panel 15. The absorbent panel 17 can be bonded to the front waist panel 13 and the rear waist panel 15 to define a three-piece construction. However, it is contemplated that an absorbent article can be manufactured in a cross-direction without being a three-piece construction garment.

The absorbent article 10, 110, 210 can have a pair of longitudinal side edges 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24. The longitudinal side edges 18, 20 can extend in a direction parallel to the longitudinal direction 30 for their entire length, such as for the absorbent articles 10, 110 illustrated in FIGS. 2 and 6. In other embodiments, the longitudinal side edges 18, 20 can be curved between the front waist edge 22 and the rear waist edge 24. In the absorbent article 210 of FIGS. 9 and 10, the longitudinal side edges 18, 20 can include portions of the front waist panel 13, the absorbent panel 17, and the rear waist panel 15.

The front waist region 12 can include the portion of the absorbent article 10, 110, 210 that, when worn, is positioned at least in part on the front of the wearer while the rear waist region 14 can include the portion of the absorbent article 10, 110, 210 that, when worn, is positioned at least in part on the back of the wearer. The crotch region 16 of the absorbent article 10, 110, 210 can include the portion of the absorbent article 10, 110, 210 that, when worn, is positioned between the legs of the wearer and can partially cover the lower torso of the wearer. The waist edges, 22 and 24, of the absorbent article 10, 110, 210 are configured to encircle the waist of the wearer and together define a central waist opening 23 (as labeled in FIG. 1 and FIG. 9) for the waist of the wearer. Portions of the longitudinal side edges 18, 20 in the crotch region 16 can generally define leg openings for the legs of the wearer when the absorbent article 10, 110, 210 is worn.

Figure 3A:
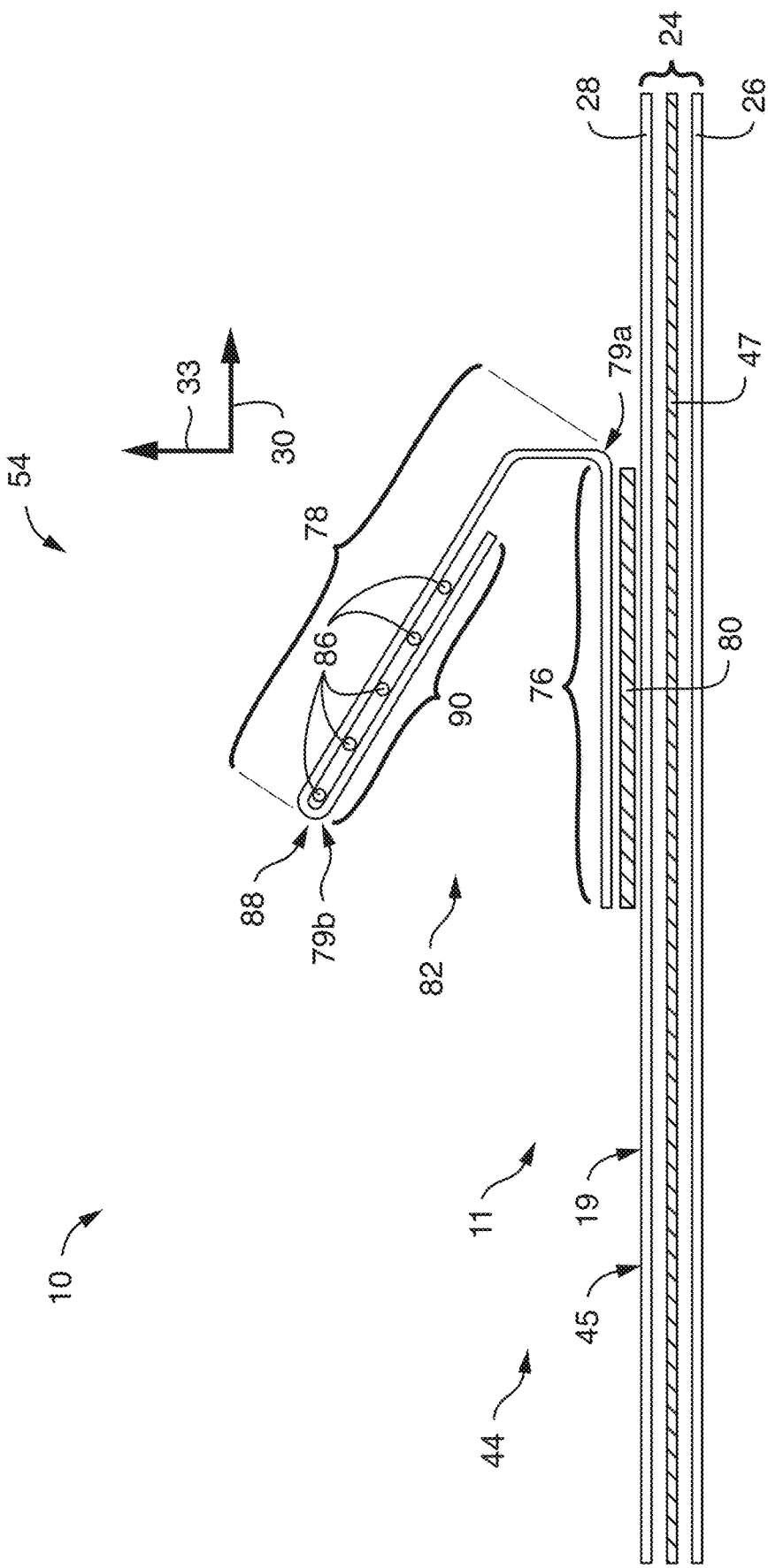
FIG. 3A is a cross-sectional view taken along line 3-3 from FIG. 2, but with the waist containment member being shown in a relaxed configuration.
Figure 3B:
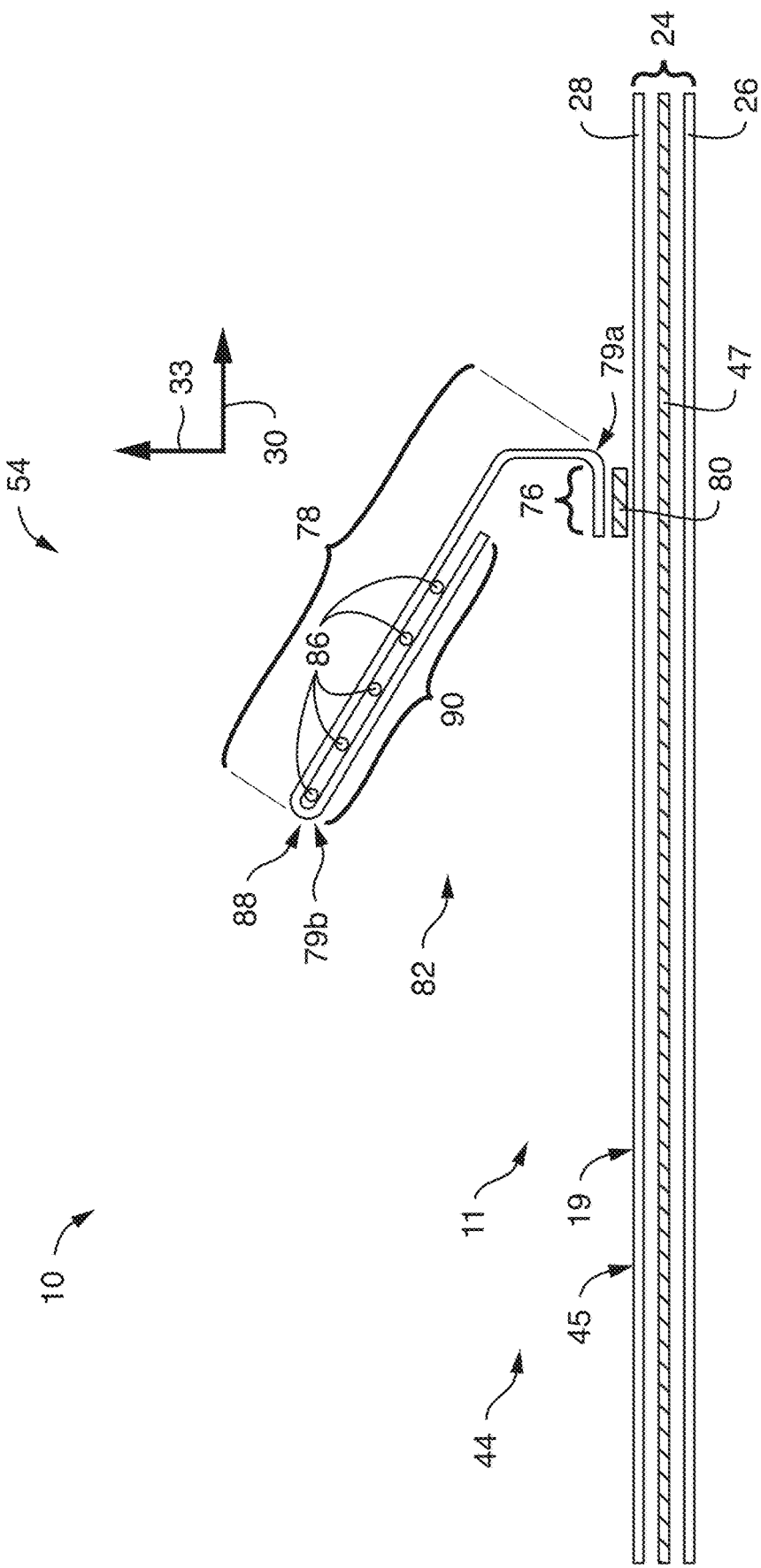
FIG. 3B is a cross-sectional view similar to FIG. 3A, but of an alternative embodiment of a waist containment member.

The absorbent article 10, 110, 210 can include an outer cover 26 and a bodyside liner 28. The outer cover 26 and the bodyside liner 28 can form a portion of the chassis 11. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. As an example, FIGS. 3A and 3B depict the bodyside liner 28 bonded to the outer cover 26 with adhesive 47. The outer cover 26 can define a length in a longitudinal direction 30, and a width in the lateral direction 32, which, in the illustrated embodiment, can coincide with the length and width of the absorbent article 10, 110. As illustrated in FIGS. 2, 6, and 10, the absorbent article 10, 110, 210 can have a longitudinal axis 29 extending in the longitudinal direction 30 and a lateral axis 31 extending in the lateral direction 32.

Figure 4:
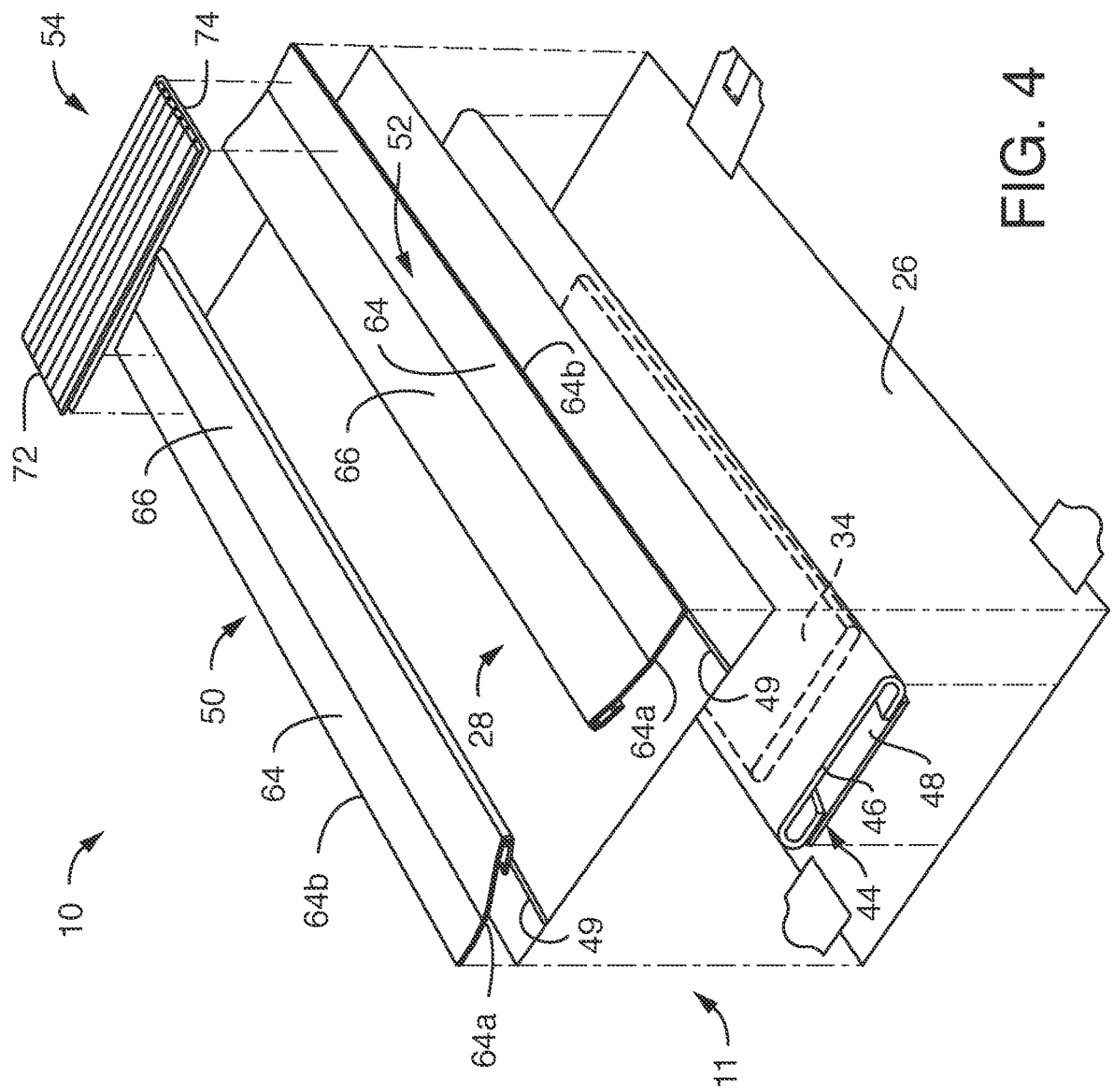
FIG. 4 is a top, side perspective, exploded view of the absorbent article of FIG. 1.
Figure 5A:
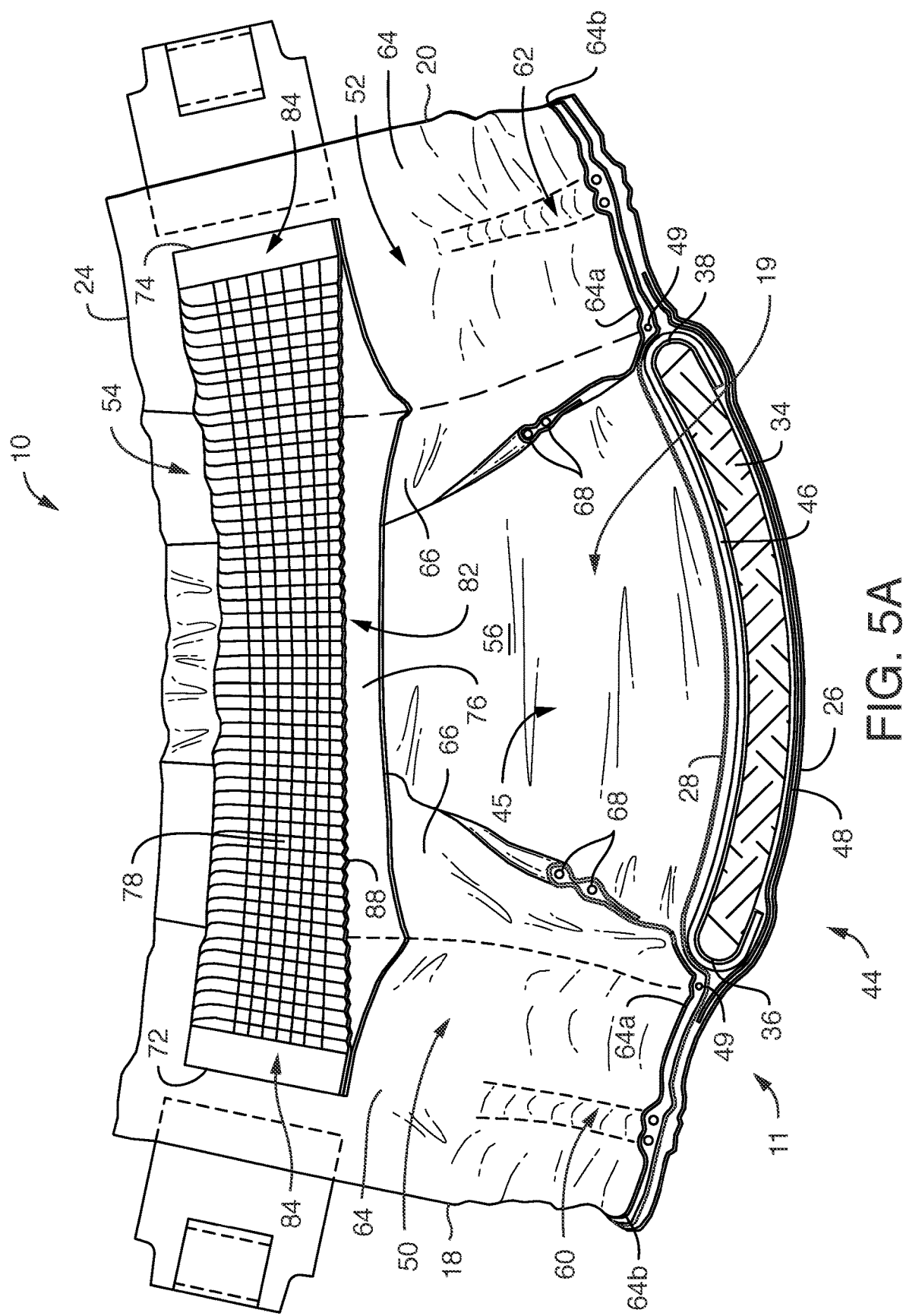
FIG. 5A is a front perspective cross-sectional view taken along line 5-5 from FIG. 2, with the absorbent article being in a relaxed configuration.
Figure 5B:
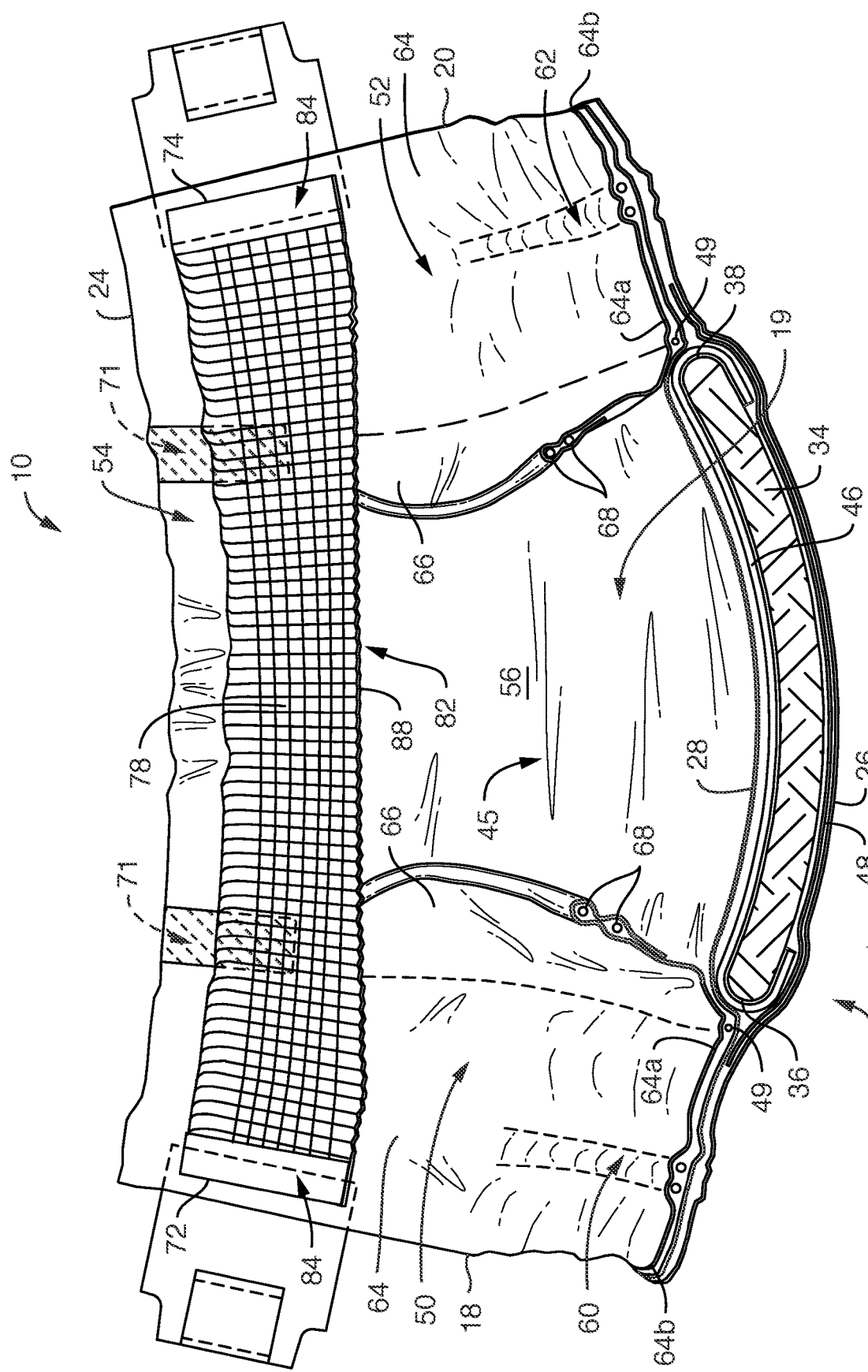
FIG. 5B is a front perspective cross-sectional view similar to FIG. 5A, but of an absorbent article including the waist containment member of FIG. 3B.

The chassis 11 can include an absorbent body 34. The absorbent body 34 can be disposed between the outer cover 26 and the bodyside liner 28. The absorbent body 34 can have longitudinal edges, 36 and 38, which, in an embodiment, can form portions of the longitudinal side edges, 18 and 20, respectively, of the absorbent article 10, 110, 210. The absorbent body 34 can have a first end edge 40 that is opposite a second end edge 42, respectively, which, in an embodiment, can form portions of the waist edges, 22 and 24, respectively, of the absorbent article 10, 110. In some embodiments, the first end edge 40 can be in the front waist region 12. In some embodiments, the second end edge 42 can be in the rear waist region 14. In an embodiment, the absorbent body 34 can have a length and width that are the same as or less than the length and width of the absorbent article 10, 110, 210. The bodyside liner 28, the outer cover 26, and the absorbent body 34 can form part of an absorbent assembly 44. In the absorbent article 210 of FIGS. 9 and 10, the absorbent panel 17 can form the absorbent assembly 44. The absorbent assembly 44 can also include a fluid transfer layer 46 (as shown in FIGS. 4, 5A, and 5B) and a fluid acquisition layer (not shown) between the bodyside liner 28 and the fluid transfer layer 46 as is known in the art. The absorbent assembly 44 can also include a spacer layer 48 (as shown in FIGS. 4, 5A, 5B, 7, and 8) disposed between the absorbent body 34 and the outer cover 26.

The absorbent article 10, 110, 210 can be configured to contain and/or absorb liquid, solid, and semi-solid body exudates discharged from the wearer. In some embodiments, containment flaps 50, 52 can be configured to provide a barrier to the lateral flow of body exudates. To further enhance containment and/or absorption of body exudates, the absorbent article 10, 110, 210 can suitably include a waist containment member 54. In some embodiments, the waist containment member 54 can be disposed in the rear waist region 14 of the absorbent article 10, 110, 210.

Although not depicted herein, it is contemplated that the waist containment member 54 can be additionally or alternatively disposed in the front waist region 12 of the absorbent article 10, 110, 210.

The waist containment member 54 can be disposed on the body facing surface 19 of the chassis 11 to help contain and/or absorb body exudates. In some embodiments, such as in the absorbent articles 10, 110 depicted in FIGS. 1-8, the waist containment member 54 can be disposed on the body facing surface 45 of the absorbent assembly 44. In some embodiments, the waist containment member 54 can be disposed on the body facing surface 56 of the bodyside liner 28. In some embodiments, such as in the absorbent article 210 depicted in FIGS. 9 and 10, the waist containment member 54 can be disposed on the body facing surface 58 of the rear waist panel 15.

The absorbent article 10, 110, 210 can further include leg elastic members 60, 62 as are known to those skilled in the art. The leg elastic members 60, 62 can be attached to the outer cover 26 and/or the bodyside liner 28 along the opposite longitudinal side edges, 18 and 20, and positioned in the crotch region 16 of the absorbent article 10, 110, 210. The leg elastic members 60, 62 can be parallel to the longitudinal axis 29 as shown in FIGS. 2, 6, and 10 or can be curved as is known in the art. The leg elastic members 60, 62 can provide elasticized leg cuffs.

In some embodiments, the absorbent article 10, 110, 210 can further include longitudinal extending fold lines 25*a*, 25*b*, as shown in FIGS. 2, 6, and 10. The first longitudinal extending fold line 25*a* can be on one side of the longitudinal axis 29 of the absorbent article 10, 110, 210 and the second longitudinal extending fold line 25*b* can be on an opposite side of the longitudinal axis 29. In some embodiments, the longitudinal extending fold lines 25*a*, 25*b* can be generally parallel to the longitudinal axis 29 of the absorbent article 10, 110, 210. In some embodiments, the absorbent article 10, 110, 210 can further include a lateral extending fold line 27. The lateral extending fold line 27 can be parallel to and located at the lateral axis 31 of the absorbent article 10, 110, 210 in some embodiments.

Additional details regarding each of these elements of the absorbent article 10, 110, 210 described herein can be found below and with reference to the FIGS. 1 through 10.

Outer Cover:

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material, such as a polymeric film. In an embodiment, the outer cover 26 can be suitably stretchable, and more suitably elastic, in at least the lateral direction 32 of the absorbent article 10, 110, 210. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In some embodiments, the outer cover 26 can be a two layer construction, including an outer layer (not shown) and an inner layer (not shown) which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The outer layer of the outer cover 26 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer of an outer cover 26 can be a 20 gsm spunbond polypropylene non-woven web. The outer layer may also be constructed of the same materials from which the bodyside liner 28 can be constructed as described herein.

The liquid impermeable inner layer of the outer cover 26 (or the liquid impermeable outer cover 26 where the outer cover 26 is of a single-layer construction) can be either vapor permeable (i.e., "breathable") or vapor impermeable. The liquid impermeable inner layer (or the liquid impermeable outer cover 26 where the outer cover 26 is of a single-layer construction) can be manufactured from a thin plastic film. The liquid impermeable inner layer (or the liquid impermeable outer cover 26 where the outer cover 26 is of a single-layer construction) can inhibit liquid body exudates from leaking out of the absorbent article 10, 110, 210 and wetting articles, such as bed sheets and clothing, as well as the wearer and caregiver.

In some embodiments, where the outer cover 26 is of a single layer construction, it can be embossed and/or matte finished to provide a more cloth-like texture or appearance. The outer cover 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. The size and the absorbent capacity of the absorbent body 34 should be compatible with the size of the intended wearer (infants to adults) and the liquid loading imparted by the intended use of the absorbent article 10, 110, 210. The absorbent body 34 can have a length and width that can be less than or equal to the length and width of the absorbent article 10, 110, 210.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In an embodiment, the absorbent body 34 may be constructed of a single layer of materials, or in the alternative, may be constructed of two or more layers of materials.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 34 can be free of superabsorbent material.

If a spacer layer 48 is present, the absorbent body 34 can be disposed on the spacer layer 48 and superposed over the outer cover 26. The spacer layer 48 can be bonded to the outer cover 26, for example, by adhesive. In some embodiments, a spacer layer 48 may not be present and the absorbent body 34 can directly contact the outer cover 26 and can be directly bonded to the outer cover 26. However, it is to be understood that the absorbent body 34 may be in contact with, and not bonded with, the outer cover 26 and remain within the scope of this disclosure. In an embodiment, the outer cover 26 can be composed of a single layer and the absorbent body 34 can be in contact with the singer layer of the outer cover 26. In some embodiments, at least a portion of a layer, such as but not limited to, a fluid transfer layer 46 and/or a spacer layer 48, can be positioned between the absorbent body 34 and the outer cover 26, such as illustrated in FIGS. 4, 5A, and 5B. The absorbent body 34 can be bonded to the fluid transfer layer 46 and/or the spacer layer 48.

Bodyside Liner:

The bodyside liner 28 of the absorbent article 10, 110, 210 can overlay the absorbent body 34 and the outer cover 26 and can isolate the wearer's skin from liquid waste retained by the absorbent body 34. In various embodiments, a fluid transfer layer 46 can be positioned between the bodyside liner 28 and the absorbent body 34. In various embodiments, an acquisition layer (not shown) can be positioned between the bodyside liner 28 and the absorbent body 34 or a fluid transfer layer 46, if present. In various embodiments, the bodyside liner 28 can be bonded to the acquisition layer, or to the fluid transfer layer 46 if no acquisition layer is present, via adhesive and/or by a point fusion bonding. The point fusion bonding may be selected from ultrasonic, thermal, pressure bonding, and combinations thereof.

Figure 7:
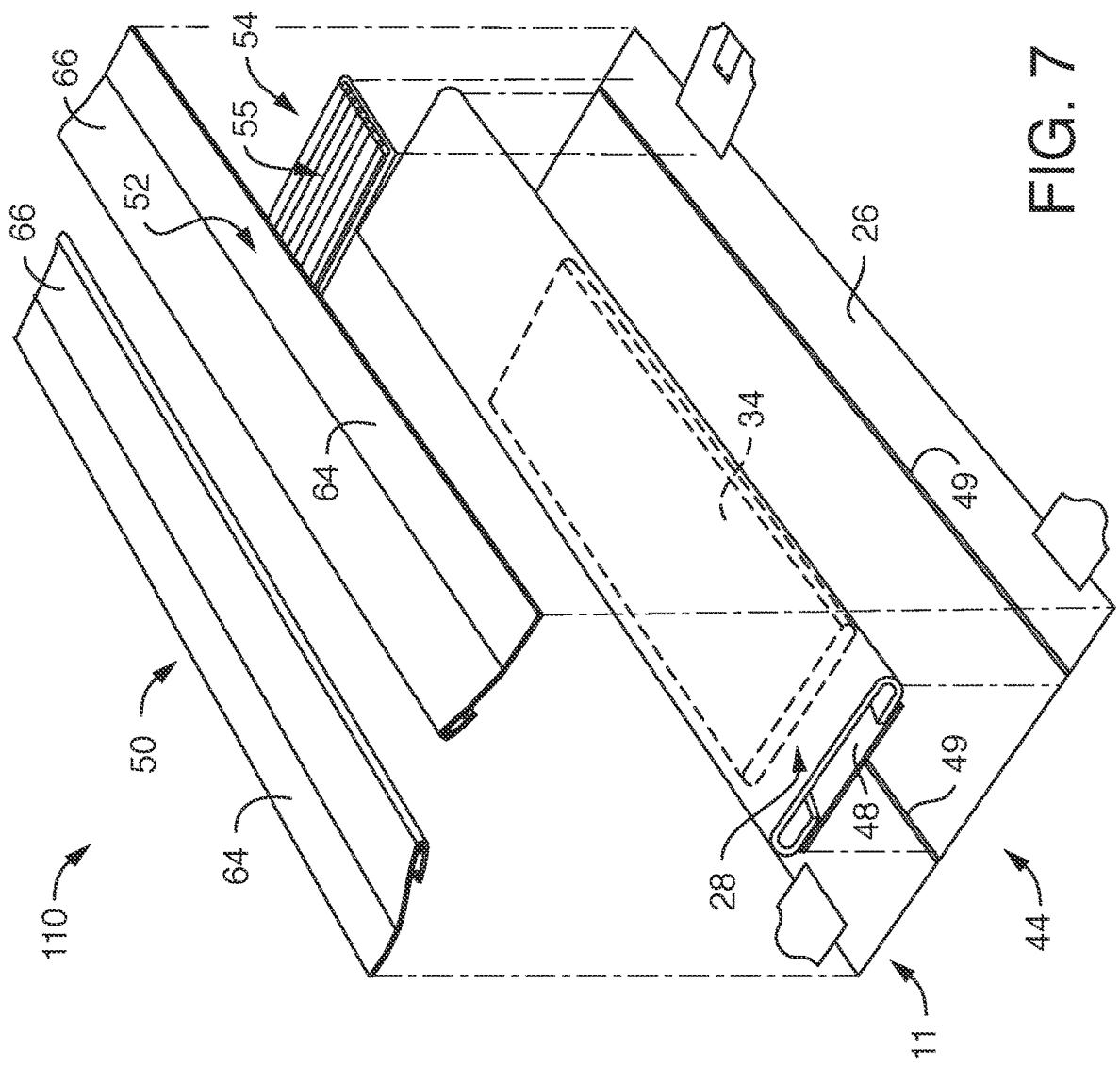
FIG. 7 is a top, side perspective, exploded view of the absorbent article of FIG. 6.
Figure 8:
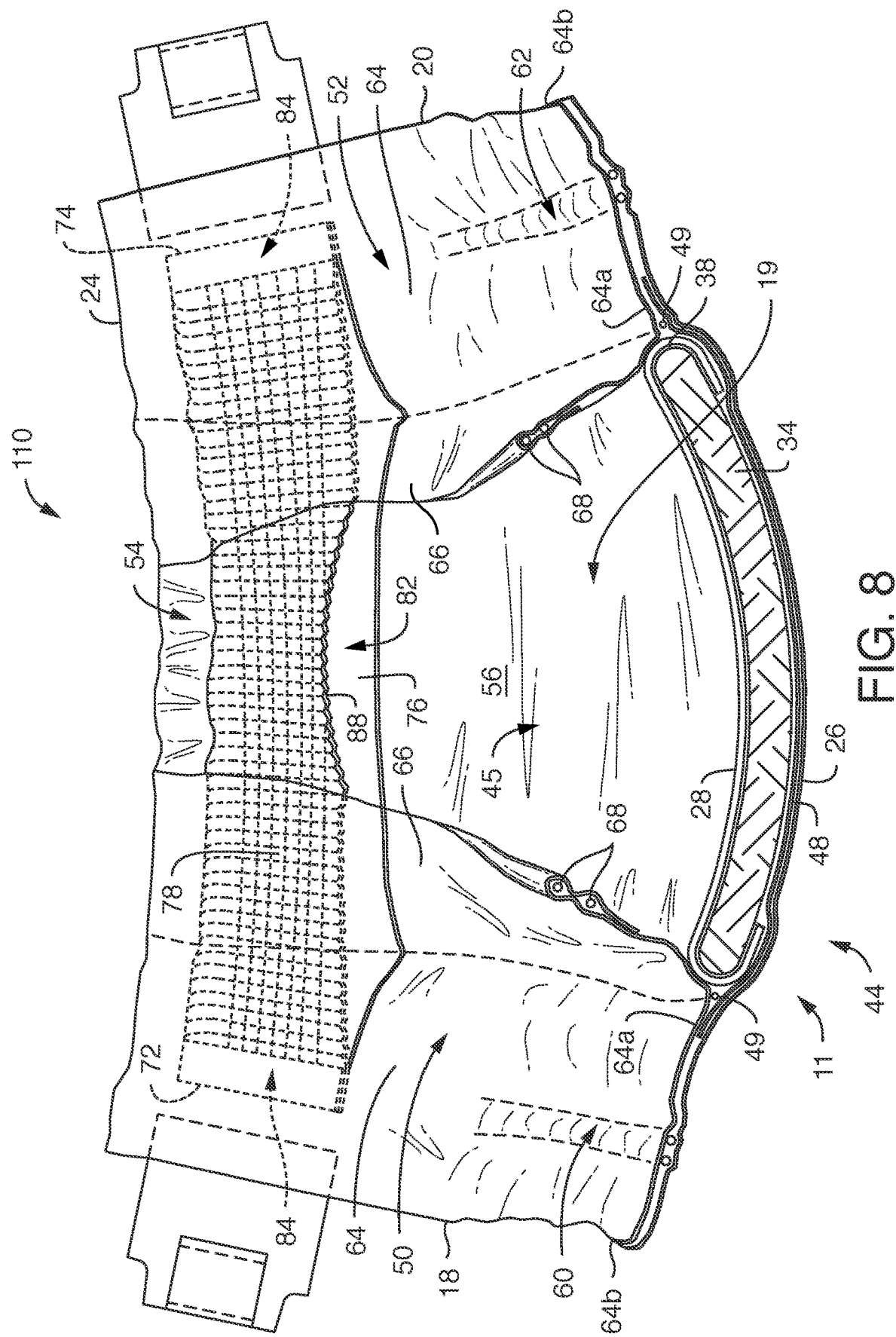
FIG. 8 is a front perspective cross-sectional view taken along line 8-8 from FIG. 6, with the absorbent article being in a relaxed configuration.

In an embodiment, the bodyside liner 28 can extend beyond the absorbent body 34 and/or a fluid transfer layer 46, if present, and/or an acquisition layer, if present, and/or a spacer layer 48, if present, to overlay a portion of the outer cover 26 and can be bonded thereto by any method deemed suitable, such as, for example, by being bonded thereto by adhesive, to substantially enclose the absorbent body 34 between the outer cover 26 and the bodyside liner 28. As illustrated in FIGS. 6-8, the bodyside liner 28 may be narrower than the outer cover 26. However, in other embodiments, the bodyside liner 28 and the outer cover 26 may be of the same dimensions in width and length, for example, as depicted in the embodiments illustrated in FIGS. 1-5B. In other embodiments, the bodyside liner 28 can be of greater width than the outer cover 26. It is also contemplated that the bodyside liner 28 may not extend beyond the absorbent body 34 and/or may not be secured to the outer cover 26. In some embodiments, such as in the absorbent article 110 illustrated in FIGS. 6-8, the bodyside liner 28 can wrap at least a portion of the absorbent body 34, including wrapping around both longitudinal edges 36, 38 of the absorbent body 34, and/or one or more of the end edges 40, 42. It is further contemplated that the bodyside liner 28 may be composed of more than one segment of material. The bodyside liner 28 can be of different shapes, including rectangular, hourglass, or any other shape. The bodyside liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, can include more than one layer of fabrics, films, and/or webs, as well as combinations thereof. For example, the bodyside liner 28 can include a support layer and a projection layer that can be hydroentagled. The projection layer can include hollow projections, such as those disclosed in U.S. Patent Application Publication No. 2014/0121623 invented by Kirby, Scott S. C. et al.

For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a spunbond substrate with a basis weight from about 10 or 12 to about 15 or 20 gsm. In an embodiment, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent article 10, 110, 210. In other aspects, the bodyside liner 28 can be stretchable, and more suitably elastic, in both the lateral and the longitudinal directions 32, 30, respectively.
Containment Flaps:

In an embodiment, the absorbent article 10, 110, 210 can include a pair of containment flaps 50, 52. The containment flaps 50, 52 can be formed separately from the absorbent chassis 11 and attached to the chassis 11 or can be formed integral to the chassis 11. In some embodiments, the containment flaps 50, 52 can be secured to the chassis 11 of the absorbent article 10, 110, 210 in a generally parallel, spaced relation with each other laterally inward of the leg openings to provide a barrier against the flow of body exudates. One containment flap 50 can be on a first side of the longitudinal axis 29 and the other containment flap 52 can be on a second side of the longitudinal axis 29. In an embodiment, the containment flaps 50, 52 can extend generally in a longitudinal direction 30 from the front waist region 12 of the absorbent article 10, 110, through the crotch region 16 to the rear waist region 14 of the absorbent article 10. In some embodiments, the containment flaps 50, 52 can extend in a direction substantially parallel to the longitudinal axis 29 of the absorbent article 10, 110, 210, however, in other embodiments, the containment flaps 50, 52 can be curved, as is known in the art. In other embodiments, such as the absorbent article 210 in FIGS. 9 and 10, the containment flaps 50, 52 can be disposed on the absorbent panel 17 in the crotch region 16.

In embodiments where the containment flaps 50, 52 are coupled to the chassis 11, the containment flaps 50, 52 can be bonded to the bodyside liner 28 with a barrier adhesive 49, as shown in FIGS. 4, 5A, and 5B, or the containment flaps 50, 52 can be bonded to the outer cover 26 with a barrier adhesive 49, as shown in FIG. 7, or to the spacer layer 48 as shown in FIG. 8. Of course, the containment flaps 50, 52 can be bonded to other components of the chassis 11 and can be bonded with other suitable means other than a barrier adhesive 49. The containment flaps 50, 52 can be constructed of a fibrous material which can be similar to the material forming the bodyside liner 28. Other conventional materials, such as polymer films, can also be employed.

The containment flaps 50, 52 can each include a base portion 64 and a projection portion 66. The base portion 64 can be bonded to the chassis 11, for example, to the bodyside liner 28 or the outer cover 26 as mentioned above. The base portion 64 can include a proximal end 64a and a distal end 64b. The projection portion 66 can be separated from the base portion 64 at the proximal end 64a of the base portion 64. As used in this context, the projection portion 66 is separated from the base portion 64 at the proximal end 64a of the base portion 64 in that the proximal end 64a of the base portion 64 defines a transition between the projection portion 66 and the base portion 64. The proximal end 64a of the base portion 64 can be located near the barrier adhesive 49. In some embodiments, the distal ends 64b of the base portion 64 can laterally extend to the respective longitudinal side edges 18, 20 of the absorbent article 10, 110, 210. In other embodiments, the distal ends 64b of the base portion 64 can end laterally inward of the respective longitudinal side edges 18, 20 of the absorbent article 10, 110, 210. The containment flaps 50, 52 can also each include a projection portion 66 that is configured to extend away from the body facing surface 19 of the chassis 11 at least in the crotch region 16 when the absorbent article 10, 110, 210 is in a relaxed configuration, as illustrated in FIGS. 5A, 5B, and 8. The containment flaps 50, 52 can include a tack-down region 71 in either or both of the front waist region 12 and the rear waist region 14 where the projection portion 66 is coupled to the body facing surface 19 of the chassis 11.

It is contemplated that the containment flaps 50, 52 can be of various configurations and shapes, and can be constructed by various methods. For example, the containment flaps 50, 52 of FIGS. 1-5A depict a vertical containment flap 50, 52 with a tack-down region 71 in both the front and rear waist regions 12, 14 where the projection portion 66 of each containment flap 50, 52 is tacked down to the bodyside liner 28 towards or away from the longitudinal axis 29 of the absorbent article 10. However, the containment flaps 50, 52 can include a tack-down region 71 such as shown in FIG. 5B where the projection portion 66 of each of the containment flaps 50, 52 is folded back upon itself and coupled to itself and the bodyside liner 28 in a "C-shape" configuration, as is known in the art and described in U.S. Pat. No. 5,895,382 to Robert L. Popp et al. As yet another alternative, it is contemplated that the containment flaps 50, 52 could be constructed in a "T-shape" configuration, such as described in U.S. patent application Ser. No. 13/900,134 by Robert L. Popp et al., which published as U.S. Patent Application Publication 2014/0350504. Such a configuration can also include a tack-down region 71 in either or both of the front and rear waist regions 12, 14, respectively. Of course, other configurations of containment flaps 50, 52 can be used in the absorbent article 10, 110, 210 and still remain within the scope of this disclosure.

The containment flaps 50, 52 can include one or more flap elastic members 68, such as the two flap elastic strands depicted in FIGS. 2, 5A, 5B, 6, and 8. Suitable elastic materials for the flap elastic members 68 can include sheets, strands or ribbons of natural rubber, synthetic rubber, or thermoplastic elastomeric materials. Of course, while two elastic members 68 are shown in each containment flap 50, 52, it is contemplated that the containment flaps 50, 52 can be configured with one or three or more elastic members 68. Alternatively or additionally, the containment flaps 50, 52 can be composed of a material exhibiting elastic properties itself.

The flap elastic members 68, as illustrated in FIGS. 2, 5A, 5B, 6, and 8, can have two strands of elastomeric material extending longitudinally in the projection portion 66 of the containment flaps 50, 52, in generally parallel, spaced relation with each other. The elastic members 68 can be within the containment flaps 50, 52 while in an elastically contractible condition such that contraction of the strands gathers and shortens the projection portions 66 of the containment flaps 50, 52 in the longitudinal direction 30. As a result, the elastic members 68 can bias the projection portions 66 of the containment flaps 50, 52 to extend away from the body facing surface 45 of the absorbent assembly 44 in a generally upright orientation of the containment flaps 50, 52, especially in the crotch region 16 of the absorbent article 10, 110, 210, when the absorbent article 10 is in a relaxed configuration.

During manufacture of the containment flaps 50, 52 at least a portion of the elastic members 68 can be bonded to the containment flaps 50, 52 while the elastic members 68 are elongated. The percent elongation of the elastic members 68 can be, for example, about 110% to about 350%. In one embodiment, the elastic members 68 can be coated with adhesive while elongated to a specified length prior to attaching to the elastic members 68 to the containment flaps 50, 52. In a stretched condition, the length of the elastic members 68 which have adhesive coupled thereto can provide an active flap elastic region 70 in the containment flaps 50, 52, as labeled in FIGS. 2 and 6, which will gather upon relaxation of the absorbent article 10, 110. The active flap elastic region 70 of containment flaps 50, 52 can be of a longitudinal length that is less than the length of the absorbent article 10, 110, 210. In this exemplary method of bonding the elastic members 68 to the containment flaps 50, 52, the portion of the elastic members 68 not coated with adhesive, will retract after the elastic members 68 and the absorbent article 10 are cut in manufacturing to form an individual absorbent article 10, 110. As noted above, the relaxing of the elastic members 68 in the active flap elastic region 70 when the absorbent article 10, 110, 210 is in a relaxed condition can cause each containment flap 50, 52 to gather and cause the projection portion 66 of each containment flap 50, 52 to extend away from the body facing surface 19 of the chassis 11 (e.g., the body facing surface 45 of the absorbent assembly 44 or the body facing surface 56 of the bodyside liner 28), as depicted in FIGS. 5A, 5B, and 8.

Of course, the elastic members 68 can be bonded to the containment flaps 50, 52 in various other ways as known by those of skill in the art to provide an active flap elastic region 70, which is within the scope of this disclosure. Additionally, the active flap elastic regions 70 can be shorter or longer than depicted herein, including extending to the front waist edge 22 and the rear waist edge 24, and still be within the scope of this disclosure.

Leg Elastics:

Leg elastic members 60, 62 can be secured to the outer cover 26, such as by being bonded thereto by laminate adhesive, generally laterally inward of the longitudinal side edges, 18 and 20, of the absorbent article 10, 110, 210. The leg elastic members 60, 62 can form elasticized leg cuffs that further help to contain body exudates. In an embodiment, the leg elastic members 60, 62 may be disposed between inner and outer layers (not shown) of the outer cover 26 or between other layers of the absorbent article 10, for example, between the base portion 64 of each containment flap 50, 52 and the bodyside liner 28 as depicted in FIGS. 5A and 5B, between the base portion 64 of each containment flap 50, 52 and the outer cover 26 as depicted in FIG. 8, or between the bodyside liner 28 and the outer cover 26. The leg elastic members 60, 62 can be one or more elastic components near each longitudinal side edge 18, 20. For example, the leg elastic members 60, 62 as illustrated herein each include two elastic strands. A wide variety of elastic materials may be used for the leg elastic members 60, 62. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Additionally, it is contemplated that the leg elastic members 60, 62 can be formed with the containment flaps 50, 52, and then attached to the chassis 11 in some embodiments. Of course, the leg elastic members 60, 62 can be omitted from the absorbent article 10, 110, 210 without departing from the scope of this disclosure.

Waist Containment Member:

In an embodiment, the absorbent article 10, 110, 210 can have one or more waist containment members 54. The waist containment member(s) 54 can be disposed in the rear waist region 14 as illustrated in FIGS. 1-10. As will be discussed in more detail below, the waist containment member 54 can help contain and/or absorb body exudates, especially low viscosity fecal matter, and as such, can be preferred to be in the rear waist region 14. In some embodiments, the absorbent article 10, 110, 210 can have a waist containment member 54 disposed in the front waist region 12. A waist containment member 54 in the front waist region 12 can help contain and/or absorb body exudates, such as urine, in the front waist region 12. Although not as prevalent as in the rear waist region 14, in some circumstances, fecal material may also spread to the front waist region 12, and thus, a waist containment member 54 disposed in the front waist region 12 can help contain and/or absorb body exudates as well. In other embodiments, the absorbent article 10, 110, 210 can have a waist containment member 54 in both the rear waist region 14 and the front waist region 12.

The waist containment member 54 can be disposed on the body facing surface 45 of the absorbent assembly 44. In some embodiments, such as in embodiments illustrated in FIGS. 1-8, the waist containment member 54 can be disposed on the body facing surface 56 of the bodyside liner 28. However, in some embodiments, such as the absorbent article 210 in FIG. 10, the waist containment member 54 can be disposed on a body facing surface 58 of the rear waist panel 15.

The waist containment member 54 can include a first longitudinal side edge 72 and a second longitudinal side edge 74. The first longitudinal side edge 72 can be opposite from the second longitudinal side edge 74. The distance between the first longitudinal side edge 72 and the second longitudinal side edge 74 can define a width 51 of the waist containment member 54 in the lateral direction 32, as shown in FIG. 2. Although not depicted, in some embodiments, the first longitudinal side edge 72 can substantially align with the first longitudinal side edge 18 of the absorbent article 10, 110, 210. Similarly, in some embodiments, the second longitudinal side edge 74 can align with the second longitudinal side edge 20 of the absorbent article 10, 110, 210. As illustrated in FIGS. 2, 5A, 5B, 6, and 8, the waist containment member 54 can be configured such that the first longitudinal side edge 72 can be disposed laterally outward of the proximal end 64a of the base portion 64 of the containment flap 50. Similarly, the waist containment member 54 can be configured such that the second longitudinal side edge 74 can be disposed laterally outward of the proximal end 64a of the base portion 64 of the containment flap 52. The waist containment member 54 can be configured such that the width 51 of the waist containment member 54 can be greater than a lateral distance between longitudinal extending fold lines 25a, 25b, as shown in FIGS. 1, 6, and 10. The first longitudinal side edge 72 can be disposed laterally outward from the first longitudinal extending fold line 25a. The second longitudinal side edge 74 can be disposed laterally outward from the second longitudinal extending fold line 25b. The longitudinal extending fold lines 25a, 25b, will be described in more detail below with respect to FIG. 13.

The waist containment member 54 can also include a proximal portion 76 and a distal portion 78. The proximal portion 76 can be coupled to the body facing surface 19 of chassis 11 (e.g., the body facing surface 45 of the absorbent assembly 44 or the body facing surface 56 of the bodyside liner 28) whereas the distal portion 78 of the waist containment member 54 can be free to move with respect to the chassis 11 and the absorbent assembly 44 when the absorbent article 10, 110, 210 is in the relaxed configuration, such as shown in FIGS. 5A, 5B, and 8. Referring to FIGS. 3A and 3B, which depict the waist containment member 54 in a relaxed configuration, the distal portion 78 can be seen extending away from the chassis 11 and absorbent assembly 44 in a vertical direction 33, which is perpendicular to the plane defined by the longitudinal axis 29 and the lateral axis 31. A fold 79a can separate the proximal portion 76 from the distal portion 78 of the waist containment member 54. As used in this context, the fold 79a separates the proximal portion 76 from the distal portion 78 in that the fold 79a defines a transition between the proximal portion 76 and the distal portion 78. The fold 79a can be created in the method 310 of manufacturing the absorbent article 10, 110, 210 including the waist containment member 54, as will be discussed in further detail below.

The proximal portion 76 can be coupled to the body facing surface 19 of the chassis 11 with an adhesive 80, and in some embodiments, the proximal portion 76 can be coupled to the body facing surface 45 of the absorbent assembly 44. In some embodiments, such as in embodiments illustrated in FIGS. 2-8, the proximal portion 76 of the waist containment member 54 can be coupled to the body facing surface 56 of the bodyside liner 28. However, in some embodiments, such as the absorbent article 210 in FIG. 10, the proximal portion 76 of the waist containment member 54 can be coupled to the body facing surface 58 of the rear waist panel 15. The proximal portion 76 can be coupled to the body facing surface 45 of the absorbent assembly 44 with adhesive 80 along the entire length of the proximal portion 76 in the longitudinal direction 30, however, it can be contemplated that only a portion of the proximal portion 76 in the longitudinal direction 30 is coupled to the body facing surface 45 of the absorbent assembly 44. Of course, it is contemplated that the proximal portion 76 of the waist containment member 54 can be coupled to the body facing surface 19 of the chassis 11 or the body facing surface 45 of the absorbent assembly 44 by means other than an adhesive 80, such as by pressure bonding, ultrasonic bonding, thermal bonding, and combinations thereof. In preferred embodiments, the proximal portion 76 is coupled to the body facing surface 19 of the chassis 11 in the lateral direction 32 in a constant fashion, as opposed to an intermittent fashion, such that a barrier to body exudates is formed between the proximal portion 76 and the body facing surface 19 of the chassis 11.

As illustrated in the embodiment depicted in FIGS. 3B and 5B, the proximal portion 76 of the waist containment member 54 can include a longitudinal length measured in the longitudinal direction 30 that is shorter than a longitudinal length of the distal portion 78 of the waist containment member 54. However, in some embodiments, the longitudinal length of the proximal portion 76 can be substantially equal to or larger than the longitudinal length of the distal portion 78 of the waist containment member 54. For purposes herein, the longitudinal length of the proximal portion 76 and the longitudinal length of the distal portion 78 of the waist containment member 54 are measured when the absorbent article 10, 110, 210 is in the stretched, laid flat configuration.

As illustrated in FIGS. 3A and 3B, because the distal portion 78 of the waist containment member 54 can freely move with respect to the absorbent assembly 44 when the absorbent article 10, 110, 210 is in the relaxed configuration, the distal portion 78 can help provide a containment pocket 82 when the absorbent article 10, 110, 210 is in the relaxed configuration. The containment pocket 82 can help provide a barrier to contain and/or can help absorb body exudates. The containment pocket 82 can be especially beneficial for containing and/or absorbing low viscosity fecal matter, which can be prevalent in younger children. The first longitudinal side edge 72 can be disposed laterally outward of the proximal end 64a of the base portion 64 of the containment flap 50, and thus, the containment pocket 82 can extend laterally outward of the proximal end 64a of the containment flap 50. Similarly, the second longitudinal side edge 74 can be disposed laterally outward of the proximal end 64a of the base portion 64 of the containment flap 52 and the containment pocket 82 can extend laterally outward of the proximal end 64a of the containment flap 52. Such a configuration provides waist containment member 54 with a wide containment pocket 82 to contain and/or absorb body exudates. To help prevent lateral flow of body exudates that are contained by the containment pocket 82 of the waist containment member 54, the distal portion 78 of the waist containment member 54 can be bonded to the proximal portion 76 of the waist containment member 54 and/or the body facing surface 19 of the chassis 11 near the first and second longitudinal side edges 72, 74, respectively. For example, FIGS. 5A, 5B, and 8 depict tack-down regions 84 where the distal portion 78 of the waist containment member 54 can be bonded to the proximal portion 76 of the waist containment member 54 and/or the body facing surface 19 of the chassis 11 near the first and second longitudinal side edges 72, 74, respectively.

In some embodiments, the width 51 of the waist containment member 54 in the lateral direction 32 as compared to the width 53 of the chassis 11 (as labeled in FIG. 2) can have a ratio of about 0.85 to about 1.00. In some embodiments, the width 51 of the waist containment member 54 in the lateral direction 32 as compared to the width 53 of the chassis 11 can have a ratio of about 0.87 to about 1.00. And in other embodiments, the width 51 of the waist containment member 54 in the lateral direction 32 as compared to the width 53 of the chassis 11 can have a ratio of about 0.90 to about 1.00. For purposes herein, the width 53 of the chassis 11 for use in this ratio is the width of the chassis 11 in the waist region in which the waist containment member 54 is disposed and both width measurements are taken in a direction parallel to the lateral direction 32. Thus, for the examples illustrated herein, the width 51 of the waist containment member 54 can be compared to the width 53 of the chassis 11 in the rear waist region 14. Additionally, the width 51 of the waist containment member 54 in the lateral direction 32 and the width 53 of the chassis 11 as discussed for the ratios herein are to be measured when the absorbent article 10, 110, 210 is in the stretched, laid flat configuration.

In preferred embodiments, the waist containment member 54 can include at least one elastic member 86. In some embodiments, such as the embodiments depicted in FIGS. 3A and 3B, the waist containment member 54 can include multiple elastic members 86, such as five elastic members 86. Of course, it is contemplated that the waist containment member 54 can include other amounts of elastic members 86. In some embodiments, the elastic members 86 can be spaced evenly in the longitudinal direction 30 in the distal portion 78 of the waist containment member 54. The elastic member 86 can span substantially from the first longitudinal side edge 72 to the second longitudinal side edge 74 of the waist containment member 54. The elastic member 86 can be disposed in the distal portion 78 of the waist containment member 54, and preferably, is located near a free edge 88 of the distal portion 78 of the waist containment member 54. As illustrated in FIGS. 3A and 3B, in some preferred embodiments, the elastic member(s) 86 can be disposed within a laminate portion 90 of the distal portion 78 of the waist containment member 54 to aid in containing the elastic member(s) 86. The laminate portion 90 can be disposed near the free edge 88 of the distal portion 78 of the waist containment member 54 and, in some embodiments, can be formed by a fold 79b in the distal portion 78 at the free edge 88. The tack-down regions 84, if present, can help retain the elastic member(s) 86, if present, in place, as well as help retain free edge 88 in place.

A wide variety of elastic materials may be used for the elastic member(s) 86 in the waist containment member 54. Suitable elastic materials can include sheets, strands or ribbons of natural rubber, synthetic rubber, elastic foams, or thermoplastic elastomeric materials (e.g., films). The elastic materials can be stretched and secured to a substrate forming the waist containment member 54, secured to a gathered substrate, or secured to a substrate and then elasticized or shrunk, for example, with the application of heat, such that the elastic retractive forces are imparted to the substrate forming the waist containment member 54.

As depicted in FIGS. 2, 6, and 10, in some embodiments the waist containment member 54 can be disposed on the body facing surface 19 of the chassis 11 such that a gap 85 is provided between the second end edge 42 of the absorbent body 34 and the free edge 88 of the distal portion 78 of the waist containment member 54. By providing a gap 85, the containment pocket 82 can have a greater void volume for body exudates. Additionally, it is believed that gap 85 can help body exudates enter the containment pocket 82 of the waist containment member 54.

The waist containment member 54 can be disposed to be coupled to the chassis 11 by being placed either over the containment flaps 50, 52 or under the containment flaps 50, 52. More specifically, as shown in FIGS. 1, 2, 4, 5A, and 5B, the waist containment member 54 can be disposed on the body facing surface 19 of the chassis 11 such that the proximal portion 76 of the waist containment member 54 is disposed over the base portion 64 of the first and the second containment flaps 50, 52, respectively. Alternatively, as illustrated in the embodiment depicted in FIGS. 6-8, the waist containment member 54 can be disposed on the body facing surface 19 of the chassis 11 such that the proximal portion 76 of the waist containment member 54 is disposed under the base portion 64 of the first and the second containment flaps 50, 52, respectively. Both configurations can provide advantages to the functioning of the waist containment member 54 to contain and/or absorb body exudates.

The embodiment where the proximal portion 76 of the waist containment member 54 is disposed over the base portion 64 of the containment flaps 50, 52 (FIGS. 1, 2, 4, 5A, and 5B) can provide the advantage that the containment flaps 50, 52 can help the distal portion 78 of the waist containment member 54 extend away from the body facing surface 45 of the absorbent assembly 44 when the absorbent article 10 is applied to the wearer. This is especially relevant where the proximal portion 76 of the waist containment member 54 has a shorter longitudinal length than the distal portion 78 of the waist containment member 54. For example, in FIGS. 3B and 5B, the flap elastics 68 in the projection portion 66 of the containment flaps 50, 52 can provide an opening force on the distal portion 78 of the waist containment member 54 when the absorbent article 10 is in the relaxed configuration and applied to the wearer, thus helping the distal portion 78 extend away from the body facing surface 45 of the absorbent assembly 44 and opening the containment pocket 82. In some embodiments, the containment pocket 82 can be additionally or alternatively opened by configuring the containment flaps 50, 52 to have an active flap elastic region 70 that longitudinally overlaps with the distal portion 78 of the waist containment member 54 when the absorbent article 10 is in the stretched, laid flat configuration, such as illustrated in FIG. 2. Additionally or alternatively, the containment pocket 82 of the waist containment member 54 can be opened by configuring the containment flaps 50, 52 to have a tack-down region 71 that does not extend from the rear waist edge 24 to the free edge 88 of the distal portion 78 of the waist containment member 54, such as illustrated in FIG. 2. However, such a configuration of the tack-down region 71 is not required, and in some embodiments, the tack-down region 71 can extend from the rear waist edge 24 past the free edge 88 of the distal portion 78 of the waist containment member 54.

The embodiment where the proximal portion 76 of the waist containment member 54 is disposed under the base portion 64 of the containment flaps 50, 52 (FIGS. 6-8) can provide the advantage of having the containment pocket 82 formed by the waist containment member 54 be free from the projection portion 66 of the containment flaps 50, 52. As shown in FIGS. 6-8, both the base portion 64 and the projection portion 66 of each containment flap 50, 52 can be coupled to the body facing surface 55 of the waist containment member 54. As a result, body exudates may more freely spread through the full width of the containment pocket 82 created by the waist containment member 54. Additionally, the coupling of the base portion 64 of the containment flaps 50, 52 to the outer cover 26 (or in some embodiments to the bodyside liner 28) can create a longitudinal barrier to the flow of body exudates out of the containment pocket 82 for exudates that spread laterally beyond the location of the barrier adhesive 49. In some embodiments, the tack-down region 71 of the projection portion 66 of each of the containment flaps 50, 52 can longitudinally overlap with the distal portion 78 of the waist containment member 54, as illustrated in FIG. 6. In some embodiments, the tack-down region 71 of projection portion 66 of each of the containment flaps 50, 52 can extend to the free edge 88 of the waist containment member 54 to further assist in containing exudates to the containment pocket 82 created by the waist containment member 54.

The waist containment member 54 can be comprised of a variety of materials. In a preferred embodiment, the waist containment member 54 can be comprised of a spunbond-meltblown-spunbond ("SMS") material. However it is contemplated that the waist containment member 54 can be comprised of other materials including, but not limited to, a spunbond-film-spunbond ("SFS"), a bonded carded web ("13CW"), or any non-woven material. In some embodiments, the waist containment member 54 can be comprised of a laminate of more than one of these exemplary materials, or other materials. In some embodiments, the waist containment member 54 can be comprised of a liquid impermeable material. In some embodiments, the waist containment member 54 can be comprised of a material coated with a hydrophobic coating. The basis weight of the material forming the waist containment member 54 can vary, however, in a preferred embodiment, the basis weight can be between about 8 gsm to about 120 gsm, not including the elastic members 86 in the waist containment member 54. More preferably, the basis weight of the material comprising the waist containment member 54 can be between about 10 gsm to about 40 gsm, and even more preferably, between about 15 gsm to about 25 gsm.

Fastening System:

In an embodiment, the absorbent article 10, 110 can include a fastening system. The fastening system can include one or more back fasteners 91 and one or more front fasteners 92. The embodiments shown in FIGS. 1, 2, and 5 depict embodiments with one front fastener 92. Portions of the fastening system may be included in the front waist region 12, rear waist region 14, or both.

The fastening system can be configured to secure the absorbent article 10, 110 about the waist of the wearer in a fastened condition as shown in FIG. 1 and help maintain the absorbent article 10, 110 in place during use. In an embodiment, the back fasteners 91 can include one or more materials bonded together to form a composite ear as is known in the art. For example, the composite fastener may be composed of a stretch component 94, a nonwoven carrier or hook base 96, and a fastening component 98, as labeled in FIGS. 2 and 6. As shown in FIG. 5B, in some embodiments the waist containment member 54 can extend to back fasteners 91. In some embodiments, the waist containment member 54 can be coupled to the stretch component 94 of the back fasteners 91, either directly or indirectly. In some embodiments, the waist containment member 54 can extend to the longitudinal side edges 18, 20 of the absorbent article 10, 110, 210.

Figure 11:
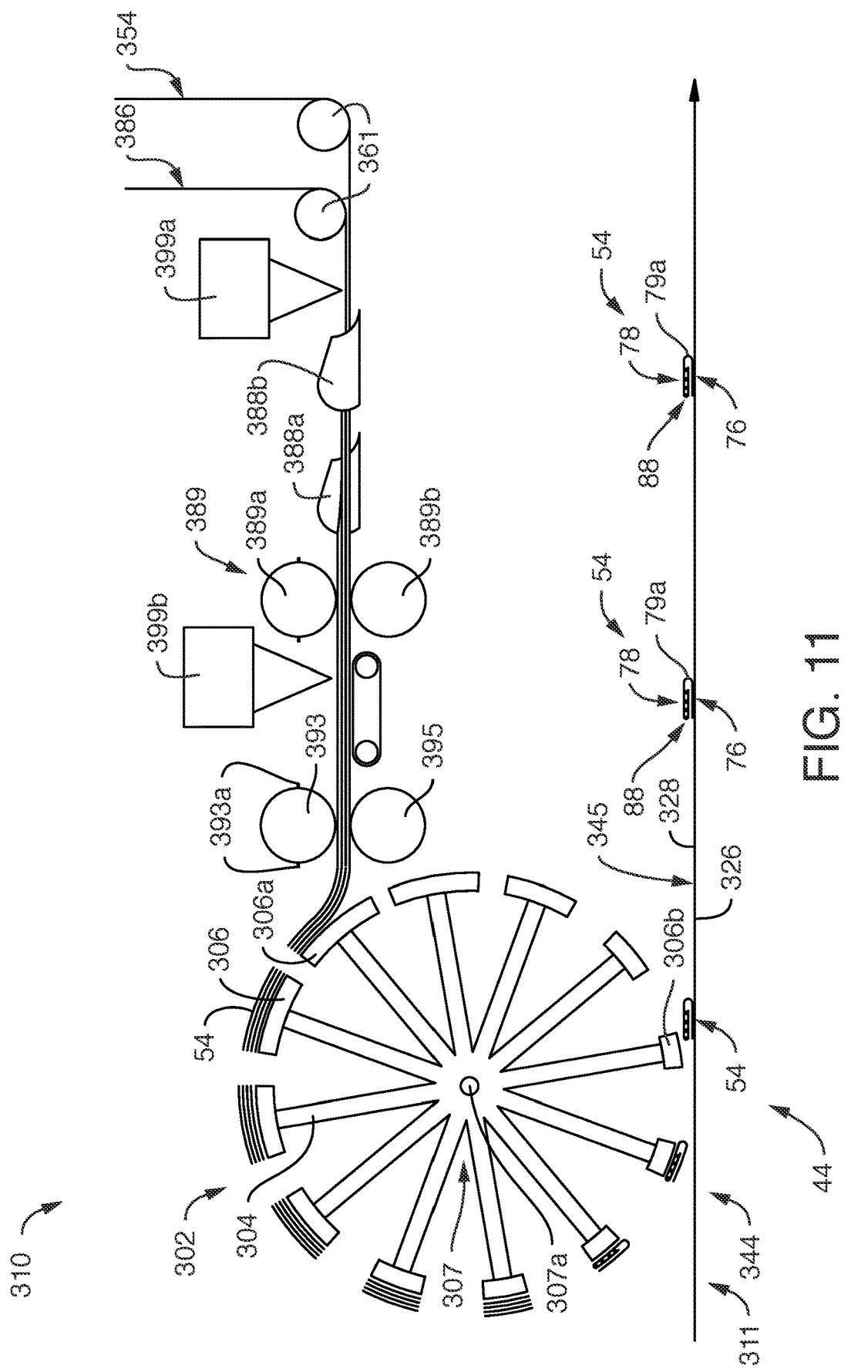
FIG. 11 is a process schematic depicting an exemplary embodiment of a method of manufacturing an absorbent article including a waist containment member.
Figure 12:
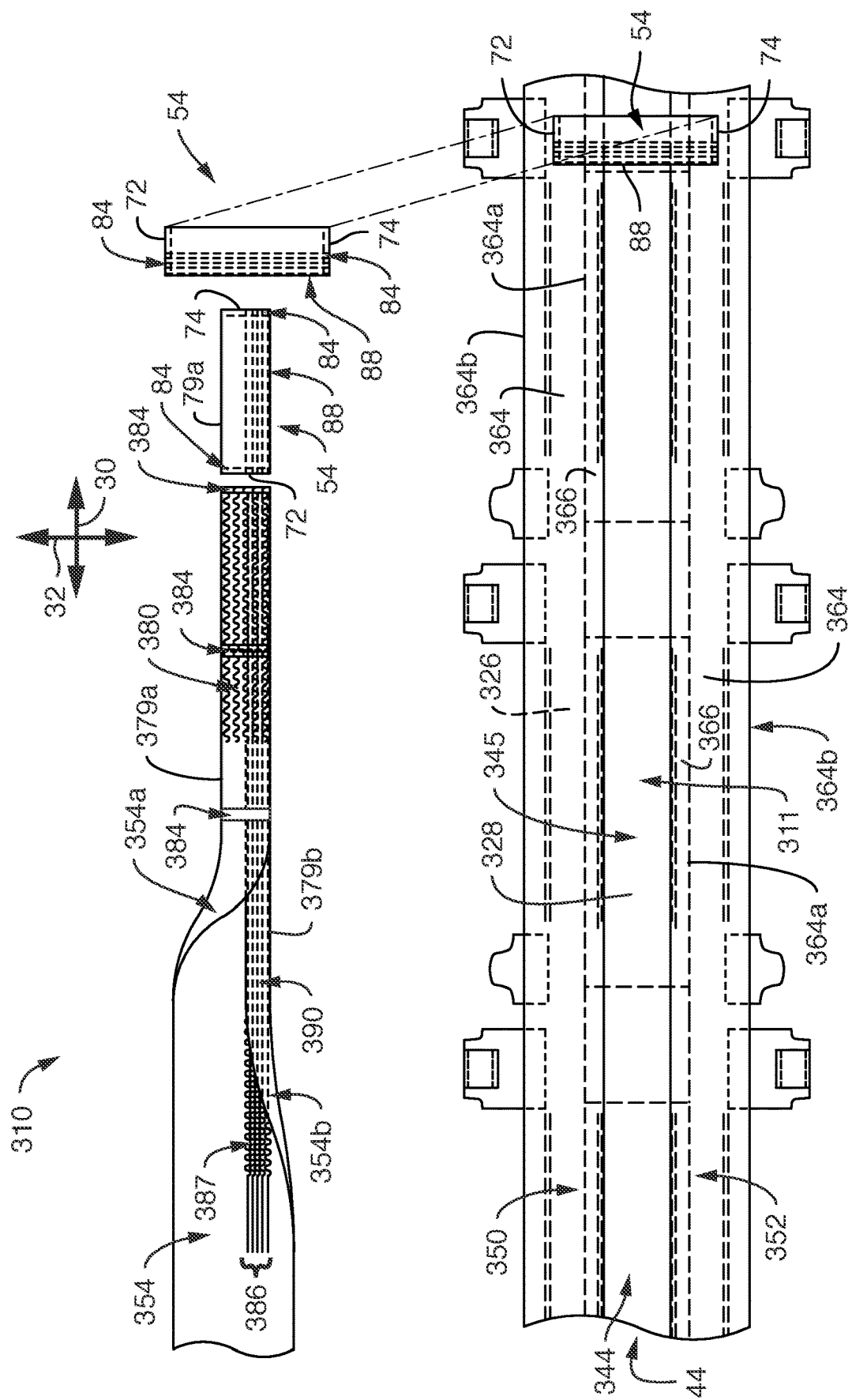
FIG. 12 is a process schematic depicting some of the steps of forming the waist containment member of the method of FIG. 11.

Method of Manufacturing an Absorbent Article:

With reference to FIGS. 11 and 12, an exemplary method 310 of manufacturing an absorbent article 10 as depicted in FIGS. 1-5B will now be described. The method 310 can include providing an absorbent assembly 44. The absorbent assembly 44 can be in a discrete form of the chassis 11 for an absorbent article 10, 110 as discussed above, or can be provided in form of an absorbent assembly web 344 as part of a chassis web 311. The absorbent assembly 44 (absorbent assembly web 344) can include a bodyside liner 28 and an outer cover 26, which can be in web form as a bodyside liner web 328 and an outer cover web 326 as well. The absorbent assembly web 344 can include a body facing surface 345.

The method 310 can include providing a pair of containment flaps 350, 352, as are discussed above, and that can each include a base portion 364 and a projection portion 366. The method 310 can also include bonding the base portion 364 of each of the containment flaps 350, 352 to the body facing surface 45 of the absorbent assembly 44 (e.g., the body facing surface 345 of the absorbent assembly web 344). In some embodiments, bonding the base portion 364 of each of the containment flaps 350, 352 to the body facing surface 45 of the absorbent assembly 44 can include bonding the base portion 364 of each of the containment flaps 350, 352 to the bodyside liner 28 (e.g., bodyside liner web 328). In other embodiments, bonding the base portion 364 of each of the containment flaps 350, 352 to the body facing surface 45 of the absorbent assembly 44 can include bonding the base portion 364 of each of the containment flaps 350, 352 to the outer cover 26 (e.g., outer cover web 326). As noted above, the base portion 364 of each of the containment flaps 350, 352 can include a proximal end 364a and a distal end 364b.

The method 310 can also include providing a continuous web of waist containment member material 354. The continuous web of waist containment member material 354 can be guided over idlers 361, as are known in the art. The continuous web of waist containment member material 354 can be folded such that at least a portion 354a of the continuous web of waist containment member material 354 is folded upon itself. Folding the continuous web of waist containment member 354 can provide a fold 379a that, once the continuous web of waist containment member 354 is cut to form a waist containment member 54, will separate the proximal portion 76 of the waist containment member 54 from the distal portion 78 of the waist containment member 54, as discussed above with respect to FIGS. 1-10. Folding the portion 354a of the continuous web of waist containment member 354 can be accomplished with a folding board 388a, as is known in the art. As is discussed above, the proximal portion 76 can be of the same or different longitudinal lengths than the distal portion 78 of the waist containment member 54, which can be accomplished by the dimensional size of portion 354a of the continuous web of waist containment member material 354.

In some embodiments, the method 310 can further include providing an elastic member 86, which can be in the form of an elastic member web 386. In some embodiments, more than one elastic member 86 can be provided. For example, in some embodiments, five elastic member webs 386 can be provided. The elastic member web(s) 386 can be bonded to the continuous web of waist containment member 354. In one embodiment, an adhesive station 399a can apply an adhesive 387 (as shown in FIG. 12) to the elastic member web(s) 386 to bond the elastic member web(s) 386 to the continuous web of waist containment member 354. The adhesive 387 can be applied in a spray fashion, or in any other suitable fashion. In some embodiments, the adhesive 387 could be applied to the continuous web of waist containment member 354 in addition to or in the place of applying the adhesive 387 to the elastic member web(s) 386.

In some embodiments, the method 310 can further include folding a portion 354b of the continuous web of waist containment member material 354 upon itself and over the elastic member web(s) 386 at fold 379b. In doing so, the continuous web of waist containment member material 354 can include a laminate portion 390 including the elastic member web(s) 386. Portion 354b of the continuous web of waist containment member material 354 can be folded upon itself and over the elastic member web(s) 386 with a folding board 388b, as is known in the art. As illustrated in FIGS. 11 and 12, the portion 354b can be folded with folding board 388b prior to the portion 354a be folded with folding board 388a.

The method 310 can also include bonding the folded continuous web of waist containment member material 354 in an intermittent fashion. Bonding the folded continuous web of waist containment member material 354 can be bonded in an intermittent fashion with bonder 389, which can create tack-down regions 384 in the folded continuous web of waist containment member material 354. The bonder 389 can include a bonding roller 389a and an anvil roller 389b. Alternatively, the tack-down regions 384 can be created in the continuous web of waist containment member material 354 using an intermittent adhesive (not shown). In such an alternative configuration, the adhesive to create the tack-down regions 384 can be applied to the continuous web of waist containment member material 354 prior to folding portion 354*a* with folding board 388*a*.

In some embodiments, the method 310 can further include applying an adhesive 380 to the continuous web of waist containment member material 354. Adhesive 380 can be applied via adhesive station 399*b*. The adhesive 380 can be applied to portion 354*a* that is folded. The adhesive 380 can bond the waist containment member 54 to the chassis 11 of the absorbent article 10 (e.g., the chassis web 311), as discussed further below.

The method 310 can additionally include cutting the continuous web of waist containment member material 354 into a discrete waist containment member 54. As illustrated in FIG. 11, the continuous web of waist containment member material 354 can be cut by a knife roll 393 including one or more knives 393*a* (two are shown in FIG. 11) and an anvil roll 395, as is known in the art. The anvil roll 395 can supply a vacuum pressure (i.e., a negative pressure) through one or more holes in the outer surface of the anvil roll 395 to help secure the continuous web of waist containment member material 354 to the anvil roll 395. The continuous web of waist containment member material 354 can be delivered to the anvil roll 395 at any suitable rate. As depicted in FIG. 12, the continuous web of waist containment member material 354 can be cut in the tack-down regions 384 to provide tack-down regions 84 for the waist containment member 54 near the first longitudinal side edge 72 and the second longitudinal side edge 74, as previously discussed.

The knife roll 393 and anvil roll 395 can cut the continuous web of waist containment member material 354 completely when each knife 393*a* comes into contact with the anvil roll 395. Alternatively, the knife roll 393 and the anvil roll 395 can be configured to perforate the continuous web of waist containment member material 354, in which case the continuous web of waist containment member material 354 can be cut at the perforations by a further separating force at a rotating module 302, which is described further below. Cutting the continuous web of waist containment member material 354 can provide a waist containment member 54 with a proximal portion 76, a distal portion 78, a first longitudinal side edge 72, and a second longitudinal side edge 74.

In some embodiments where an absorbent article 10, 110 is manufactured in a machine direction process, the method 310 can include rotating the waist containment member 54 about 90 degrees after cutting the waist containment member 54 from the continuous web of waist containment member material 354. For example, in a preferred embodiment, a rotating module 302 can rotate the waist containment member 54. The general construction and operation of such a rotating module 302 is well known and is exemplified by U.S. Pat. Nos. 5,716,478 and 5,759,340 issued to Boothe et al. and U.S. Pat. No. 6,139,004 issued to Couillard et al., each of which is incorporated herein by reference in its entirety to the extent not inconsistent herewith. The rotating module 302 can include a plurality of transfer arms 304 (twelve transfer arms 304 are shown in FIG. 11) and a plurality of transfer pucks 306 (twelve transfer pucks 306 are shown in FIG. 11). The rotating module 302 can include a rotating means 307, such as a shaft 307*a* that can be directly or indirectly driven by a drive motor or other suitable means (not shown) as is conventionally used for such equipment. Thus, the rotation shaft 307*a* can propel the transfer arms 304 about an axis such that the transfer pucks 306 can transfer the waist containment members 54 from the anvil roll 395 to the chassis 11 (e.g., chassis web 311). If the knife roll 393 and anvil roll 395 are configured to perforate the continuous web of waist containment member material 354, the rotating module 302 can be configured to cut the continuous web of waist containment member material 354 at the perforations made by the knife roll 393 by applying a force to the continuous web of waist containment member material 354 when a transfer puck 306 picks up the continuous web of waist containment member material 354 and begins to transfer the continuous web of waist containment member material 354 at a faster speed than the anvil roll 395.

Each of the transfer pucks 306 can be coupled to a respective transfer arm 304. The transfer pucks 306 can be equipped with conventional vacuum assist or other means (not shown) to allow the transfer pucks 306 to pick up the waist containment members 54 (or continuous web of waist containment member material 354) from the knife roll 393 and the anvil roll 395. Each of the transfer pucks 306 is equipped with conventional means to pivot about the longitudinal axis of the respective transfer arm 304 so that each of the transfer pucks 306 are rotatable or pivotable between a first position when the transfer pucks 306 first receive the waist containment member 54 (or the continuous web of waist containment member material 354), such as shown by transfer puck 306*a* in FIG. 11, and a second position where the transfer pucks 306 transfer the waist containment member 54 to the chassis 11 (e.g., the chassis web 311), such as shown by transfer puck 306*b*. The transfer pucks 306 can rotate 90° from the first position (such as shown by transfer puck 306*a*) to the second position (such as shown by transfer puck 306*b*).

As illustrated in FIGS. 11 and 12, the waist containment member 54 is rotated about 90° by the rotating module 302 prior to bonding the waist containment member 54 to the chassis 11 (e.g., chassis web 311) to form containment member 54 on the absorbent article 10, 110. It is contemplated, however, that in some embodiments no rotation of the waist containment member 54 is necessary. For example, if a cross-direction manufacturing process is utilized to provide an absorbent article, such as the absorbent article of FIGS. 9 and 10 discussed herein, then no rotation of the waist containment member 54 may be included in method 310.

The method 310 can also include bonding the waist containment member 54 to the chassis 11 (e.g., chassis web 311). The waist containment member 54 can be bonded to the chassis 11 (e.g., chassis web 311) by the adhesive 380 applied to the portion 354*a* of the continuous web of waist containment member material 354, as discussed above. The waist containment member 54 can be bonded to the body facing surface 19 of the chassis 11 (e.g., chassis web 311). The waist containment member 54 can be bonded to the body facing surface 45 of the absorbent assembly 44 (e.g., the body facing surface 345 of the absorbent assembly web 344). In a preferred embodiment, the method 310 can include bonding the waist containment member 54 to the body facing surface 45 of the absorbent assembly 44 such that the first longitudinal side edge 72 of the waist containment member 54 is disposed laterally outward of the proximal end 364*a* of the base portion 364 of the containment flap 350 and the second longitudinal side edge 74 of the waist containment member 54 is disposed laterally outward of the proximal end 364*a* of the base portion 364 of the containment flap 352, as illustrated in FIG. 12.

It is to be noted that if the proximal portion 76 of the waist containment member 54 is to be disposed above the base portion 364 of the containment flaps 350, 352, then the waist containment member 54 can be bonded to the body facing surface 19 of the chassis 11 (e.g., the body facing surface 345 of the absorbent assembly web 344) after the base portion 364 of the containment flaps 350, 352 are bonded to the body facing surface 19 of the chassis 11 (e.g., body facing surface 345 of the absorbent assembly web 344), as is illustrated in the exemplary method 310 shown in FIGS. 11 and 12. Such a configuration can provide an absorbent article 10 such as illustrated in FIGS. 1, 2, and 5A. It can be appreciated, however, that if the proximal portion 76 of the waist containment member 54 is to be disposed under the base portion 364 of the containment flaps 350, 352, then the waist containment member 54 can be bonded to the body facing surface 19 of the chassis 11 (e.g., the body facing surface 345 of the absorbent assembly web 344) before the base portion 364 of the containment flaps 350, 352 are bonded to the body facing surface 19 of the chassis 11 (e.g., body facing surface 345 of the absorbent assembly web 344). Such a configuration can provide an absorbent article 110 such as illustrated in FIGS. 6-8.

If the chassis 11 is provided in the form of a chassis web 311, the method 310 can also include cutting the chassis web 311 to form individual absorbent articles. In one embodiment, cutting the chassis web 311 can be done with a cutoff module (not shown) as is known in the art.

Figure 13:
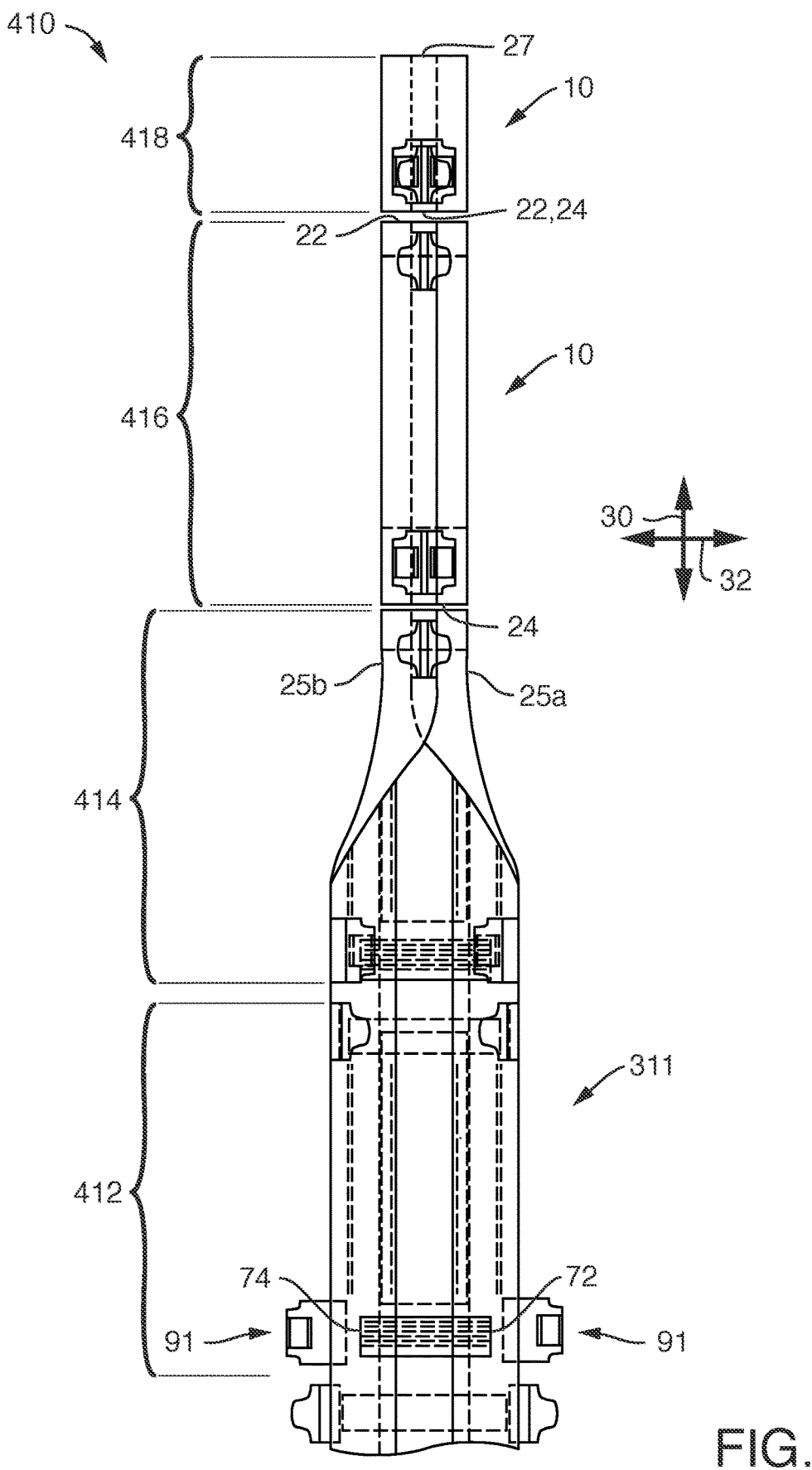
FIG. 13 is a process schematic depicting a folding process for folding an absorbent article, such as the absorbent article of FIG. 1.

FIG. 13 illustrates one suitable folding process 410 for an exemplary absorbent article, such as the absorbent articles 10, 110 as discussed herein that can be manufactured in a machine direction process. The folding process 410 is merely exemplary, and it is contemplated that the absorbent articles 10, 110, 210 described herein may not be folded at all, or may be folded by another suitable folding process. As seen in FIG. 13, the absorbent article 10 may be constructed from a chassis web 311, similar to that as illustrated and discussed with respect to FIGS. 11 and 12. The chassis web 311 can be folded as depicted and then separated into individual absorbent articles 10, for example, with a cutoff module (not shown) as is well known in the art. It is understood that the individual absorbent articles 10 can be separated from the chassis web 311 prior to the absorbent article 10 being folded.

The depicted folding process 410 of FIG. 13 comprises a series of folding steps 412, 414, 416, 418 to move the absorbent article 10 from a substantially flat configuration (e.g., as depicted in FIG. 2) to a folded configuration, such as shown in step 418. In the first folding step 412, the back fasteners 91 are folded over on themselves. More particularly, in the first folding step 412 the outermost portions of the back fasteners 91 (i.e., portions of the back fasteners 91 comprising the hook base 96 and the fastener 98, as labeled in FIG. 2) are folded toward the bodyside liner 28. In some embodiments, the portion of each back fastener 91 folded over in step 412 may engage another portion of the corresponding the back fastener 91 which is not folded over. If the absorbent article 10 includes front ears (not labeled), they can be folded over in step 412 as well.

In the second folding step 414, the back fasteners 91 can be folded interior to the chassis 11 (e.g., chassis web 311). In the second folding step 414, the chassis 11 (e.g., chassis web 311) is folded along the longitudinal extending fold lines 25a, 25b, starting in what will become the front waist region 12 of an absorbent article 10. The chassis 11 (e.g., the chassis web 311) can continue to be folded along longitudinal extending fold lines 25a, 25b in what will become the rear waist region 14 of the absorbent article 10. In some embodiments, the absorbent article 10 can be folded such that the longitudinal edges 18, 20 in the front waist region 12 overlap one another near a longitudinal axis 29 of the absorbent article 10 (all components as labeled in FIG. 2) in second folding step 414. In folding the chassis 11 along the longitudinal extending fold lines 25a, 25b, the waist containment member 54 can also be folded. For example, as illustrated in FIG. 2, and as discussed above, if the first longitudinal side edge 72 and the second longitudinal side edge 74 of the waist containment member 354 are each disposed laterally outward of the first longitudinal extending fold line 25a and the second longitudinal extending fold line 25b, respectively, then the portions of the waist containment member 54 laterally outside of the longitudinal extending fold lines 25a, 25b can be folded.

As seen in FIG. 13, at the third folding step 416, the absorbent article 10 can be separated from the chassis web 311, e.g., cutting the absorbent article 10 along the rear waist edge 24 of the leading absorbent article 10 and along the front waist edge 22 of the trailing absorbent article 10. The absorbent article 10 may be cut from the chassis web 311 in the third step 416 by any suitable means well known in the art.

At the fourth folding step 418, the absorbent article 10 is folded at or near a lateral fold line 27 such that the rear waist edge 24 is generally aligned with the front waist edge 22 in the folded state. The lateral fold line 27 can be aligned with the lateral axis 31 of the absorbent article 10, as labeled in FIG. 2. In such a folded state, the absorbent article 10 is well suited for packaging as is well known in the art. For example, the folded absorbent article 10 may be stacked with like folded diapers and provided in consumer packaging for retail sale.

Benefits can be provided to a waist containment member 54 in a folded absorbent article 10 that is configured such that the waist containment member 54 is wider than the longitudinal extending fold lines 25a, 25b, or in other words, such that the first longitudinal side edge 72 is disposed laterally outward from the first longitudinal extending fold line 25a and the second longitudinal side edge 74 is disposed laterally outward from the second longitudinal extending fold line 25b. When the absorbent article 10 is unfolded along longitudinal extending fold lines 25a, 25b, the waist containment member 54 can help open the containment pocket 82 formed by the waist containment member 54 when the absorbent article 10 is in a relaxed configuration. This is especially true for embodiments that include one or more elastic members 86 in the waist containment member 54 that extend laterally beyond the longitudinal extending fold lines 25a, 25b. In such a configuration, the elastic members 86 can contract after the absorbent article 10 is unfolded along longitudinal extending fold lines 25a, 25b and when the absorbent article 10 is put in a relaxed configuration, such as illustrated in FIGS. 5A and 5B. Additionally, for embodiments of the waist containment member 54 including one or more elastic members 86 extending laterally beyond the longitudinal extending fold lines 25a, 25b, the elastic members 86 can be in a contracted state when the absorbent article 10 is in a folded configuration, such as shown in the fourth step 418 in FIG. 13. Because the absorbent article 10 may be in this configuration for some time between manufacturing of the absorbent article 10 and use of the absorbent article 10 by the wearer, configuring the waist containment member 54 to allow the elastic members 86 to rest in a contracted state can prevent the retractive forces of the elastic members 86 from diminishing over time, and thus, can preserve the beneficial properties of the elastic members 86 of the waist containment member 54 for when the absorbent article 10 is being worn by a wearer.

As noted above, it is contemplated that other processes of folding the absorbent articles 10, 110, 210 described herein can be used other than the folding process 410 described above and illustrated in FIG. 13. It is contemplated that other folding processes can achieve the benefits to the waist containment member 54 noted above by folding the absorbent article 10 along longitudinal extending fold lines 25a, 25b. Furthermore, it is also within the scope of this disclosure that no folding of the absorbent articles 10, 110, 210 is required.

Embodiments

Embodiment 1: An absorbent article including a front waist region, a rear waist region, a crotch region, a longitudinal axis and a lateral axis, the absorbent article comprising: a chassis including an absorbent body, the chassis including a body facing surface and a garment facing surface; a pair of containment flaps including a first containment flap and a second containment flap, the first containment flap being on a first side of the longitudinal axis and the second containment flap being on a second side of the longitudinal axis, the first and second containment flap each comprising: a base portion including a proximal end and a distal end; and a projection portion configured to extend away from the body facing surface of the chassis in at least the crotch region when the absorbent article is in a relaxed configuration; and a waist containment member disposed on the body facing surface of the chassis, the waist containment member comprising: a first longitudinal side edge and a second longitudinal side edge, the first longitudinal side edge being disposed laterally outward of the proximal end of the base portion of the first containment flap, the second longitudinal side edge being disposed laterally outward of the proximal end of the base portion of the second containment flap; a proximal portion, the proximal portion being coupled to the body facing surface of the chassis; and a distal portion, a fold separating the distal portion from the proximal portion, the distal portion of the waist containment member being free to move with respect to the chassis when the absorbent article is in the relaxed configuration.

Embodiment 2: An absorbent article including a front waist region, a rear waist region, a crotch region, a longitudinal axis and a lateral axis, the absorbent article comprising: a chassis including an absorbent body, the chassis including a body facing surface and a garment facing surface; and a waist containment member disposed on the body facing surface of the chassis, the waist containment member comprising: a first longitudinal side edge and a second longitudinal side edge, the first longitudinal side edge being disposed on a first side of the longitudinal axis and the second longitudinal edge being disposed on a second side of the longitudinal axis; a proximal portion, the proximal portion being coupled to the body facing surface of the chassis; and a distal portion, a fold separating the distal portion from the proximal portion, the distal portion of the waist containment member being free to move with respect to the chassis, the waist containment member including a first width in the lateral direction and the chassis including a second width in the lateral direction, a ratio of the first width to the second width is about 0.85 to about 1.00.

Embodiment 3: A folded absorbent article including a front waist region, a rear waist region, a crotch region, a longitudinal axis and a lateral axis, the absorbent article comprising: a chassis including an absorbent body, the chassis including a body facing surface and a garment facing surface; a pair of longitudinally extending fold lines including a first longitudinally extending fold line and a second longitudinally extending fold line, the first longitudinally extending fold line being on a first side of the longitudinal axis and the second longitudinally extending fold line being on a second side of the longitudinal axis; and a waist containment member disposed on the body facing surface of the chassis, the waist containment member comprising: a first longitudinal side edge and a second longitudinal side edge, the first longitudinal side edge being disposed laterally outward of the first longitudinally extending fold line and the second longitudinal side edge being disposed laterally outward of the second longitudinally extending fold line; a proximal portion, the proximal portion being coupled to the body facing surface of the chassis; and a distal portion, a fold separating the distal portion from the proximal portion, the distal portion of the waist containment member being free to move with respect to the chassis.

Embodiment 4: The absorbent article of embodiment 2 or embodiment 3, further comprising: a pair of containment flaps including a first containment flap and a second containment flap, the first containment flap being on the first side of the longitudinal axis and the second containment flap being on the second side of the longitudinal axis, the first and second containment flap each comprising: a base portion including a proximal end and a distal end; and a projection portion configured to extend away from the body facing surface of the chassis in at least the crotch region when the absorbent article is in a relaxed condition, the projection portion being separated from the base potion at the proximal end of the base portion.

Embodiment 5: The absorbent article of embodiment 1 or embodiment 4, wherein the waist containment member provides a containment pocket for containing exudates, the containment pocket extending laterally outward of the proximal end of the base portion of the first containment flap and laterally outward of the base portion of the proximal end of the second containment flap.

Embodiment 6: The absorbent article of any of the preceding embodiments, wherein the chassis further comprises a bodyside liner and an outer cover, the absorbent body being disposed between the bodyside liner and the outer cover.

Embodiment 7: The absorbent article of embodiment 6, wherein the bodyside liner includes a body facing surface, and wherein the proximal portion of the waist containment member is coupled to the body facing surface of the bodyside liner.

Embodiment 8: The absorbent article of embodiment 1, wherein the proximal portion of the waist containment member is disposed over the base portion of the first and second containment flaps.

Embodiment 9: The absorbent article of embodiment 4, wherein the proximal portion of the waist containment member is disposed over the base portion of the first and second containment flaps.

Embodiment 10: The absorbent article of embodiment 1, wherein the proximal portion of the waist containment member is disposed under the base portion of the first and second containment flaps.

Embodiment 11: The absorbent article of embodiment 4, wherein the proximal portion of the waist containment member is disposed under the base portion of the first and second containment flaps.

Embodiment 12: The absorbent article of any one of the preceding embodiments, wherein the distal portion of the waist containment member is coupled to the proximal portion of the waist containment member near the first longitudinal side edge and the second longitudinal side edge of the waist containment member.

Embodiment 13: The absorbent article of any one of the preceding embodiments, wherein the waist containment member further comprises at least one elastic member.

Embodiment 14: The absorbent article of embodiment 13, wherein the at least one elastic member spans substantially from the first longitudinal side edge to the second longitudinal side edge of the waist containment member.

Embodiment 15: The absorbent article of embodiment 13, wherein the at least one elastic member is coupled to the distal portion of the waist containment member near a free edge of the distal portion.

Embodiment 16: The absorbent article of any one of embodiments 1-3, wherein the waist containment member further comprises at least one elastic member, and wherein the distal portion of the waist containment member includes a laminate portion, the laminate portion being near a free edge of the distal portion and including the at least one elastic member.

Embodiment 17: The absorbent article of embodiment 1, wherein the proximal portion includes a longitudinal length as measured in a direction parallel the longitudinal axis when the absorbent article is in a stretched, laid flat configuration and the distal portion includes a longitudinal length as measured in the direction parallel to the longitudinal axis when the absorbent article is in a stretched, laid flat configuration, the longitudinal length of the proximal portion being less than the longitudinal length of the distal portion.

Embodiment 18: The absorbent article of embodiment 4, wherein the proximal portion includes a longitudinal length as measured in a direction parallel the longitudinal axis when the absorbent article is in a stretched, laid flat configuration and the distal portion includes a longitudinal length as measured in the direction parallel to the longitudinal axis when the absorbent article is in a stretched, laid flat configuration, the longitudinal length of the proximal portion being less than the longitudinal length of the distal portion.

Embodiment 19: The absorbent article of embodiment 17, wherein the proximal portion of the waist containment member is disposed over the base portion of the first and second containment flaps, the first and second containment flaps each comprise an active flap elastic region, and wherein the active flap elastic region of each of the first and second containment flaps longitudinally overlaps the distal portion of the waist containment member when the absorbent article is in the stretched, laid flat configuration.

Embodiment 20: The absorbent article of embodiment 1, wherein the proximal portion of the waist containment member is disposed under the base portion of the first and second containment flaps, the projection portion of each of the first and second containment flaps comprises a tack-down region, and wherein the tack-down region of each of the first and second containment flaps longitudinal overlaps with the distal portion of the waist containment member when the absorbent article is in a stretched, laid flat configuration.

Embodiment 21: The absorbent article of embodiment 4, wherein the proximal portion of the waist containment member is disposed under the base portion of the first and second containment flaps, the projection portion of each of the first and second containment flaps comprises a tack-down region, and wherein the tack-down region of each of the first and second containment flaps longitudinal overlaps with the distal portion of the waist containment member when the absorbent article is in a stretched, laid flat configuration.

Embodiment 22: The absorbent article of any one of the preceding embodiments, wherein the distal portion includes a free edge, the absorbent body includes a first end edge and a second end edge opposite the first end edge, the second end edge being closer to the waist containment member than is the first end edge, and wherein a gap is provided between the free edge of the distal portion of the waist containment member and the second end edge of the absorbent body.

Embodiment 23: The absorbent article of any one of the preceding embodiments, wherein the waist containment member is disposed in the rear waist region.

Embodiment 24: A method of manufacturing an absorbent article, the absorbent article including a front waist region, a rear waist region, a crotch region, a longitudinal axis and a lateral axis, the method comprising: providing an absorbent assembly including a bodyside liner, an outer cover, and an absorbent body disposed between the bodyside liner and the outer cover, the absorbent assembly including a body facing surface; providing a pair of containment flaps including a first containment flap and a second containment flap, the first containment flap and the second containment flap each including a base portion and a projection portion; bonding the base portion of each of the first and the second containment flaps to the body facing surface of the absorbent assembly, the base portion of each of the first and the second containment flaps each including a proximal end and a distal end; providing a continuous web of waist containment member material; folding at least a portion of the continuous web of waist containment member material upon itself; cutting the continuous web of waist containment member material to provide a waist containment member including a proximal portion, a distal portion, a first longitudinal side edge, and a second longitudinal side edge, the folding of the at least a portion of the continuous web of waist containment member material providing a separation between the distal portion of the waist containment member and the proximal portion of the waist containment member; and bonding the proximal portion of the waist containment member to the body facing surface of the absorbent assembly such that the first longitudinal side edge of the waist containment member is disposed laterally outward of the proximal end of the base portion of the first containment flap and the second longitudinal side edge of the waist containment member is disposed laterally outward of the proximal end of the base portion of the second containment flap, the distal portion of the waist containment member being free to move with respect to the proximal portion of the waist containment member when the absorbent article is in the relaxed configuration.

Embodiment 25: The method of manufacturing an absorbent article of embodiment 24, the method further comprising: providing an elastic member; and bonding the elastic member to the continuous web of waist containment member material, the elastic member being located in the distal portion of the waist containment member.

Embodiment 26: The method of manufacturing an absorbent article of embodiment 24 or embodiment 25, the method further comprising: rotating the waist containment member about 90 degrees after cutting the continuous web of waist containment member material to provide the waist containment member and prior to bonding the proximal portion of the waist containment member to the body facing surface of the absorbent assembly.

Embodiment 27: The method of manufacturing an absorbent article of any one of embodiments 24-26, wherein the waist containment member is bonded to the body facing surface of the absorbent assembly after the base portion of each of the first and second containment flaps is bonded to the body facing surface of the absorbent assembly, such that the proximal portion of the waist containment member is disposed over the base portion of the first and second containment flaps.

Embodiment 28: The method of manufacturing an absorbent article of any one of embodiments 24-26, wherein the waist containment member is bonded to the body facing surface of the absorbent assembly before the base portion of each of the first and the second containment flaps is bonded to the body facing surface of the absorbent assembly, such that the proximal portion of the waist containment member is disposed under the base portion of the first and second containment flaps.

Embodiment 29: The method of manufacturing an absorbent article of any one of embodiments 24-28, further comprising intermittently bonding the continuous web of waist containment member material to itself prior to cutting the continuous web of waist containment member material to provide tack-down regions near the first longitudinal side edge and the second longitudinal side edge of the waist containment member after the continuous web of waist containment member material is cut.

Embodiment 30: The method of manufacturing an absorbent article of any one of embodiments 24-29, further comprising folding the absorbent article at a first longitudinal extending fold line and a second longitudinal extending fold line, the first longitudinal extending fold line being configured such that the first longitudinal side edge of the waist containment member is disposed laterally outside of the first longitudinal extending fold line and the second longitudinal extending fold line being configured such that the second longitudinal side edge of the waist containment member is disposed laterally outside of the second longitudinal extending fold line.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article including a front waist region, a rear waist region, a crotch region, a longitudinal axis and a lateral axis, the absorbent article comprising:
   a chassis including a bodyside liner, an outer cover, and an absorbent body disposed between the bodyside liner and the outer cover, the chassis including a body facing surface and a garment facing surface and having a first chassis longitudinal side edge and a second chassis longitudinal side edge;
   a pair of containment flaps including a first containment flap and a second containment flap, the first containment flap being on a first side of the longitudinal axis and the second containment flap being on a second side of the longitudinal axis, the first and second containment flap each comprising:
   a base portion coupled to the chassis, the base portion including a proximal end and a distal end, and
   a projection portion configured to extend away from the body facing surface of the chassis in at least the crotch region when the absorbent article is in a relaxed configuration, the projection portion further comprising tack-down regions in the front waist region and the rear waist region where the projection portion is bonded to the body facing surface of the chassis; and
   a waist containment member disposed on the body facing surface of the chassis, the waist containment member comprising:
   a proximal portion coupled to the body facing surface of the chassis, the proximal portion overlapping, in a vertical direction perpendicular to the longitudinal axis and the lateral axis, a tack-down region of the projection portion of each containment flap, and
   a distal portion comprising a distal free edge, the distal portion and distal free edge of the waist containment member being free to move with respect to the chassis when the absorbent article is in the relaxed configuration, and the distal free edge being disposed closer to the lateral axis than the tack-down regions of the containment flaps which vertically overlap the proximal portion, and
   wherein the waist containment member comprises a fold separating the distal portion from the proximal portion, the fold vertically overlapping the tack-down region of the projection portion of each containment flap.

2. The absorbent article of claim 1, wherein the distal portion of the waist containment member is bonded to the proximal portion of the waist containment member at a first tack-down region and a second tack-down region, the first tack-down region and the second tack down region being disposed laterally outward of the tack-down regions of the projection portions of the containment flaps.

3. The absorbent article of claim 2, wherein the first tack-down region and the second tack down region being disposed laterally inward of the side edges of the chassis.

4. The absorbent article of claim 1, wherein the proximal portion is coupled to the projection portion of each containment flap with the projection portion of each containment flap disposed between the proximal portion and the bodyside liner.

5. The absorbent article of claim 1, wherein the proximal portion is disposed between the projection portion of each containment flap and the bodyside liner.

6. The absorbent article of claim 1, wherein the distal free edge of the distal portion is disposed between the tack-down regions of the projection portions of the containment flaps which vertically overlap the proximal portion and the absorbent body.

7. The absorbent article of claim 1, wherein the distal portion of the waist containment member further comprises at least one elastic member, the at least one elastic member being disposed between the tack-down regions of the projection portions of the containment flaps which vertically overlap the proximal portion and the absorbent body.

8. The absorbent article of claim 1, wherein the waist containment member has a first width in the lateral direction and the chassis has a second width in the lateral direction, a ratio of the first width to the second width is greater than about 0.85.

9. The absorbent article of claim 1, further including a pair of longitudinally extending fold lines for folding the absorbent article into a folded configuration, the fold lines comprising a first longitudinally extending fold line and a second longitudinally extending fold line, the first longitudinally extending fold line being on a first side of the longitudinal axis and the second longitudinally extending fold line being on a second side of the longitudinal axis, wherein a first longitudinal side edge of the waist containment member is disposed laterally outward of the first longitudinally extending fold line and a second longitudinal side edge of the waist containment member is disposed laterally outward of the second longitudinally extending fold line.

10. The absorbent article of claim 1, wherein the proximal portion is free of elastic members.

11. An absorbent article including a front waist region, a rear waist region, a crotch region, a longitudinal axis and a lateral axis, the absorbent article comprising:
   a chassis including a bodyside liner, an outer cover, and an absorbent body disposed between the bodyside liner and the outer cover, the chassis including a body facing surface and a garment facing surface and having a first chassis longitudinal side edge and a second chassis longitudinal side edge;
   a pair of containment flaps including a first containment flap and a second containment flap, the first containment flap being on a first side of the longitudinal axis and the second containment flap being on a second side of the longitudinal axis, the first and second containment flap each comprising:
      a base portion coupled to the chassis, the base portion including a proximal end and a distal end, and
      a projection portion configured to extend away from the body facing surface of the chassis in at least the crotch region when the absorbent article is in a relaxed configuration, the projection portion further comprising tack-down regions in the front waist region and the rear waist region where the projection portion is bonded to the body facing surface of the chassis; and
   a waist containment member disposed on the body facing surface of the chassis and overlapping, in a vertical direction perpendicular to the longitudinal axis and the lateral axis, a tack-down region of the projection portion of each containment flap, the waist containment member extending between waist containment member longitudinal side edges and further comprising:
      a proximal portion coupled to the body facing surface of the chassis, the proximal portion being free of elastic members, and
      a distal portion comprising a distal free edge and a plurality of elastics extending between the waist containment member longitudinal side edges, wherein the distal portion and distal free edge of the waist containment member being free to move with respect to the chassis when the absorbent article is in the relaxed configuration and wherein at least some of the plurality of elastics are disposed closer to the lateral axis than the tack-down regions of the containment flaps.

12. The absorbent article of claim 11, wherein the waist containment member comprises a fold separating the distal portion from the proximal portion, the fold vertically overlapping the tack-down region of the projection portion of each containment flap.

13. The absorbent article of claim 11, wherein the distal portion comprises a distal free edge and the distal free edge is disposed closer to the lateral axis than the tack-down regions of the containment flaps which vertically overlap the waist containment member.

14. The absorbent article of claim 11, wherein a free edge of the distal portion of the waist containment member is disposed closer to the lateral axis than a fold separating the distal portion from the proximal portion.

15. The absorbent article of claim 14, wherein the proximal portion includes a longitudinal length as measured in a direction parallel the longitudinal axis when the absorbent article is in a stretched, laid flat configuration and the distal portion includes a longitudinal length as measured in the direction parallel to the longitudinal axis when the absorbent article is in a stretched, laid flat configuration, the longitudinal length of the proximal portion being less than the longitudinal length of the distal portion.

16. The absorbent article of claim 11, wherein the distal portion of the waist containment member is bonded to the proximal portion of the waist containment member at a first tack-down region and a second tack-down region, the first tack-down region disposed laterally outward of the proximal end of the base portion of the first containment flap and the second tack-down region disposed laterally outward of the proximal end of the of base portion of the second containment flap, and wherein the distal portion is unbonded to the proximal portion between the first tack-down region and the second tack-down region.

17. The absorbent article of claim 11, wherein the waist containment member has a first width in the lateral direction and the chassis has a second width in the lateral direction, a ratio of the first width to the second width is greater than about 0.85.

18. The absorbent article of claim 11, further including a pair of longitudinally extending fold lines for folding the absorbent article into a folded configuration, the fold lines comprising a first longitudinally extending fold line and a second longitudinally extending fold line, the first longitudinally extending fold line being on a first side of the longitudinal axis and the second longitudinally extending fold line being on a second side of the longitudinal axis, wherein a first longitudinal side edge of the waist containment member is disposed laterally outward of the first longitudinally extending fold line and a second longitudinal side edge of the waist containment member is disposed laterally outward of the second longitudinally extending fold line.

* * * * *